US008939887B2

(12) United States Patent
Morrell et al.

(10) Patent No.: US 8,939,887 B2
(45) Date of Patent: Jan. 27, 2015

(54) COMPOSITION FOR SEPARATING SPERMATOZOA FROM A SEMEN SAMPLE

(76) Inventors: Jane Morrell, Uppsala (SE); Heriberto Rodriguez-Martinez, Göteborg (SE)

(*) Notice: Subject to any disclaimer, the term of this patent is extended or adjusted under 35 U.S.C. 154(b) by 1128 days.

(21) Appl. No.: 12/677,034

(22) PCT Filed: Sep. 5, 2008

(86) PCT No.: PCT/SE2008/050997
§ 371 (c)(1),
(2), (4) Date: Apr. 14, 2010

(87) PCT Pub. No.: WO2009/031970
PCT Pub. Date: Mar. 12, 2009

(65) Prior Publication Data
US 2011/0004051 A1 Jan. 6, 2011

(30) Foreign Application Priority Data
Sep. 7, 2007 (SE) .................................... 0701999

(51) Int. Cl.
*A61B 17/43* (2006.01)
*C12N 1/02* (2006.01)
(Continued)

(52) U.S. Cl.
CPC . *C12N 1/02* (2013.01); *A61K 35/52* (2013.01); *C12N 5/061* (2013.01); *C12N 5/0612* (2013.01)
USPC .......................................................... 600/35

(58) Field of Classification Search
CPC ..... A61D 19/00; A61D 19/02; A61D 19/021; A61D 19/022; A61D 19/024; A61D 19/025; A61D 19/027; A61D 19/028; A61D 19/04; A61M 31/00
USPC .......................................... 600/33–35; 435/2
See application file for complete search history.

(56) References Cited

U.S. PATENT DOCUMENTS 5,840,502 A * 11/1998 Van Vlasselaer ............ 435/7.21
2003/0186212 A1 * 10/2003 Loskutoff et al. ................ 435/2
(Continued)

OTHER PUBLICATIONS

Zhang et al., "Separation of High-quality Sperm by PureSperm Centrifugation Applied to Intrauterine Insemination Cycles", National Journal of Andrology, May 2004, pp. 348-350, vol. 10, No. 5, XP002612956.
(Continued)

*Primary Examiner* — Samuel Gilbert
(74) *Attorney, Agent, or Firm* — Young & Thompson

(57) ABSTRACT

Compositions and methods useful for processing animal semen for use in assisted reproduction. A composition, or colloid formulation, for separation of spermatozoa from a semen sample, the composition including at least one salt of an alkali metal and/or an alkaline earth metal, EDTA, a zwitterion buffer, silane-coated silica particles and water, the composition having a pH of 7.0-7.35 and an osmolarity of 300-345 mOsm. A method for preparing spermatozoa from a semen sample from a non-human animal by separating the spermatozoa from other semen constituents by centrifugation through a single layer of the composition, or colloid formulation. Also, a method for separating a sperm sub-population of interest from a semen sample from a non-human animal by providing a density gradient comprising at least two layers of the composition of the invention, each layer having a different density; separating the sperm sub-populations in the semen sample by centrifugation through the density gradient; and selecting the sperm sub-population of interest. Finally, spermatozoa prepared by these methods and the use of such spermatozoa in artificial insemination, in vitro fertilisation or intracytoplasmic sperm injection.

33 Claims, 18 Drawing Sheets

(51) Int. Cl.
  *A61K 35/52* (2006.01)
  *C12N 5/076* (2010.01)
  *C12N 5/071* (2010.01)

(56) References Cited

U.S. PATENT DOCUMENTS

2004/0073964 A1* 4/2004 Ellington et al. ............... 800/21
2005/0079480 A1* 4/2005 Loskutoff ........................ 435/2
2012/0263694 A1* 10/2012 Lennox et al. ............. 424/93.45

OTHER PUBLICATIONS

Morrell et al., "Techniques for Sperm Clean-up and Selection of Stallion Spermatozoa", Animal Reproduction Science, Sep. 2008, pp. 333-334, vol. 107, No. 3-4, Elsevier Science Publishers, Amsterdam, NL, XP022931556.
Morrell et al., "Prolongation of Stallion Sperm Survival by Centrifugation through Coated Silica Colloids: A Preliminary Study", Animal Reproduction, Jul. 2008, pp. 121-126, vol. 5, No. 3-4, XP002612957.
Mortimer D., "Sperm Preparation Methods", Journal of Andrology, May 2000, pp. 357-366, vol. 21, No. 3, J. B. Lippincott Co., Philadelphia, USA, XP001018042.
Morrell et al., "Comparison of Density Gradient and Single Layer Centrifugation of Stallion Spermatozoa: Yield, Motility and Survival", Equine Veterinary Journal, Jan. 2009, pp. 53-58, vol. 41, No. 1, XP002612958.
Morrell et al., "Single-layer centrifugation with Androcoll-E can be scaled up to allow large volumes of stallion ejaculate to be processed easily", Theriogenology, Oct. 2009, pp. 879-884, vol. 72, No. 6, Los Altos, CA, USA, XP026521993.
EP Search Report dated Dec. 7, 2010, in corresponding EP08829030.
Colenbrander, B. et al: The predictive value of semen analysis in the evaluation of stallion fertility, 2003, Reprod. Dom Anim 38, 305-311.
Malmgren, L: Effectiveness of two systems for transporting equine semen, 1998, Theriogenology 50, 833-839.
Samardzija, M et al: A comparison of BoviPure and Percoll on bull sperm separation protocols for IVF, 2006, Anim Reprod Sci 3-4, 237-247.
MacPherson, M et al: Use of a silane-coated silica particle solution to enhance the quality of ejaculated semen in stallions, 2002, Theriogenology 58, 317-320.
Morrell J.M.: Update on semen technologies for animal breeding, 2006, Reprod. DomAnim. 40, 1-5.
Kenney R et al: Minimal contamination techniques for breeding mares: techniques and preliminary findings. Proc. Am. Assoc. Equine Practice 1975;21,327-336.
Williams W et al: Technique of collecting semen for laboratory examination with review of several diseased bulls. (1920) Cornell Vet 10,87-94.
Evenson, DP., Darzynkiewicz, Z & Melamed, M.R. (1980) Relation of mammalian sperm chromatin heterogeneity to fertility. Science 210,1131-1133.
Januskauskas, A et al: (2001) Assessment of sperm quality through fluorimetry and sperm chromatin structure assay in relation to file fertility of frozen-thawed semen from Swedish AI-bulls. Theriogenology 55, 947-961.
Januskauskas a et al: Subtle membrane changes in cryopreserved bull semen in relation to sperm viability, chromatin structure and field fertility, 2003, Theriogenology 60:743-758.
Kavak, A et al: Evaluation of cryopreserved stallion semen from Tori and Estonian breeds using CASA and flow cytometry, 2003, Anim Reprod Sci 76: 205216.
Saravia F et al: Cooling during semen cryopreservation does not induce capacitation of boar spermatozoa, 2007, Int J Andro130: 485-499.
Tejerina F et al: Assessment of motility of ejaculated, liquid-stored boar spermatozoa using computerized instruments. Theriogenology 2008;69; 1129-1138.
Tanghe S et al: Assessment of different sperm quality parameters to predict in vitro fertility of bulls, 2002, Reprod Domest Anim 37, 127-132.
Ponglowhapen S et al: Influence of glucose and fructose in the extender during long-term storage of chilled canine semen, 2004, Theriogenolgy 62, 1498-1517.
Morrel JM., Updated on semen technologies for animal breeding, Reprod Dom Anim 2006, 41: p. 63-67.
Puresperm 40/80. Datasheet [online]. Serpentem Aeneum Co, 2003 [retrieved on Feb. 29, 2008], Retrieved from the internet: <URL: http://serpentem.co.kr/product/puresperm/40_80.html>.
Loomis P.R. Advanced methods for handling and preparation of stallion semen. Vet Clin Equine 2006, 22: 663-676.
Dominick J. et al., Improved Sperm recovery by hyperosmotic percoll gradient., J of Assisted Reproduction and Genetics 1997, 14, 394-397.
International Search Report dated Dec. 18, 2008, from corresponding PCT application.

* cited by examiner

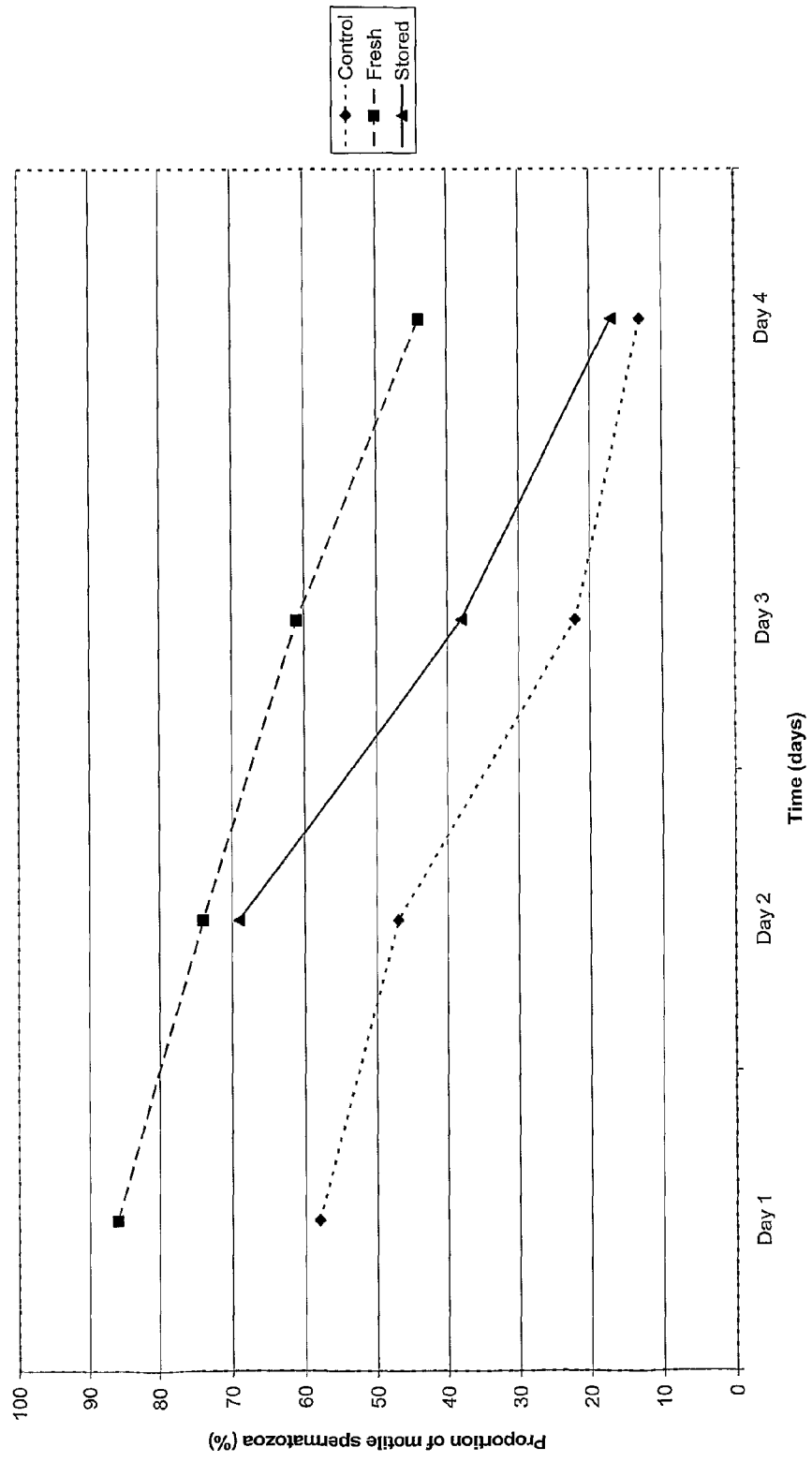

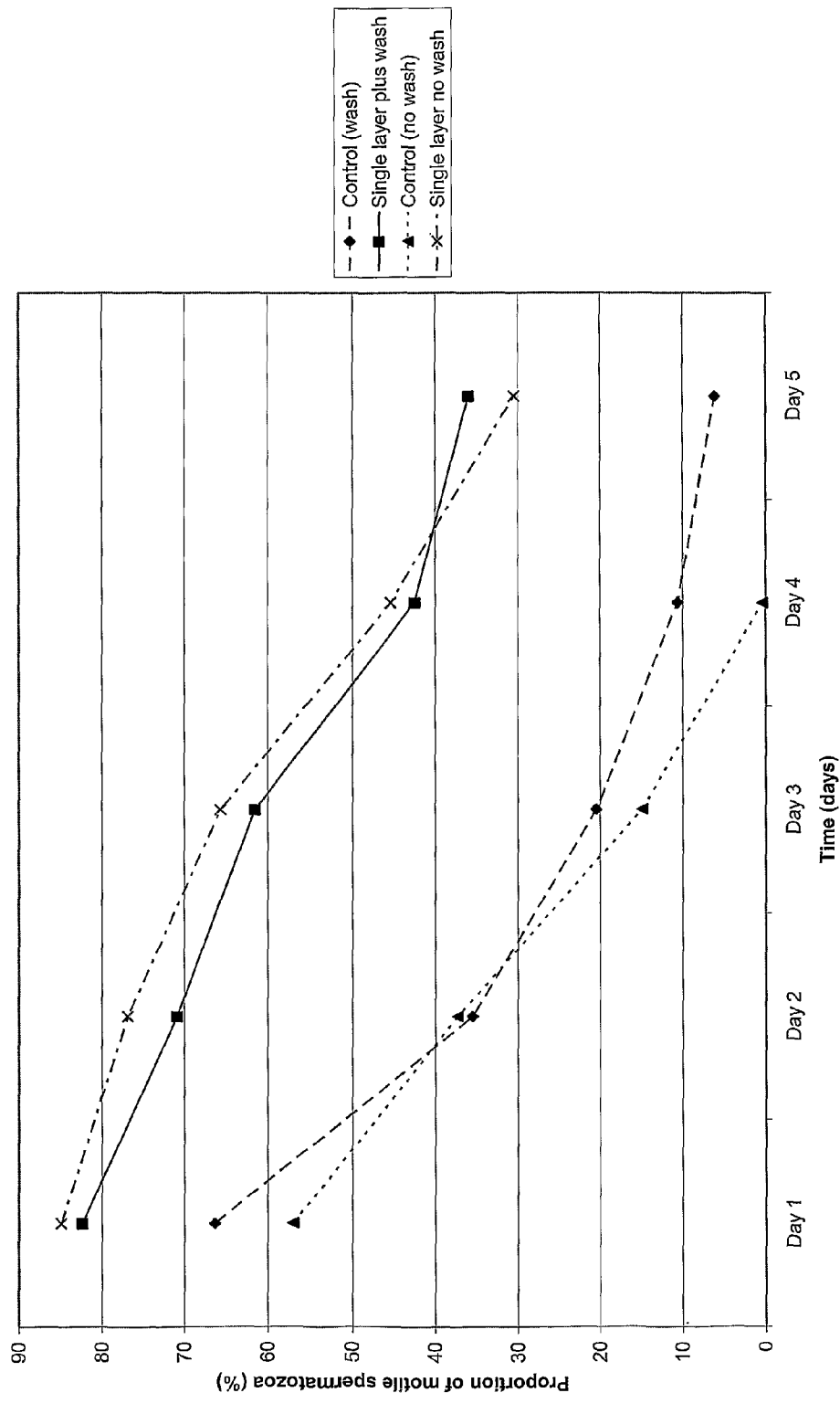
Figure 2: effect of washing (n=38) or not washing (n=38) the sperm pellet after single layer centrifugation on mean subjective motility estimates (%).

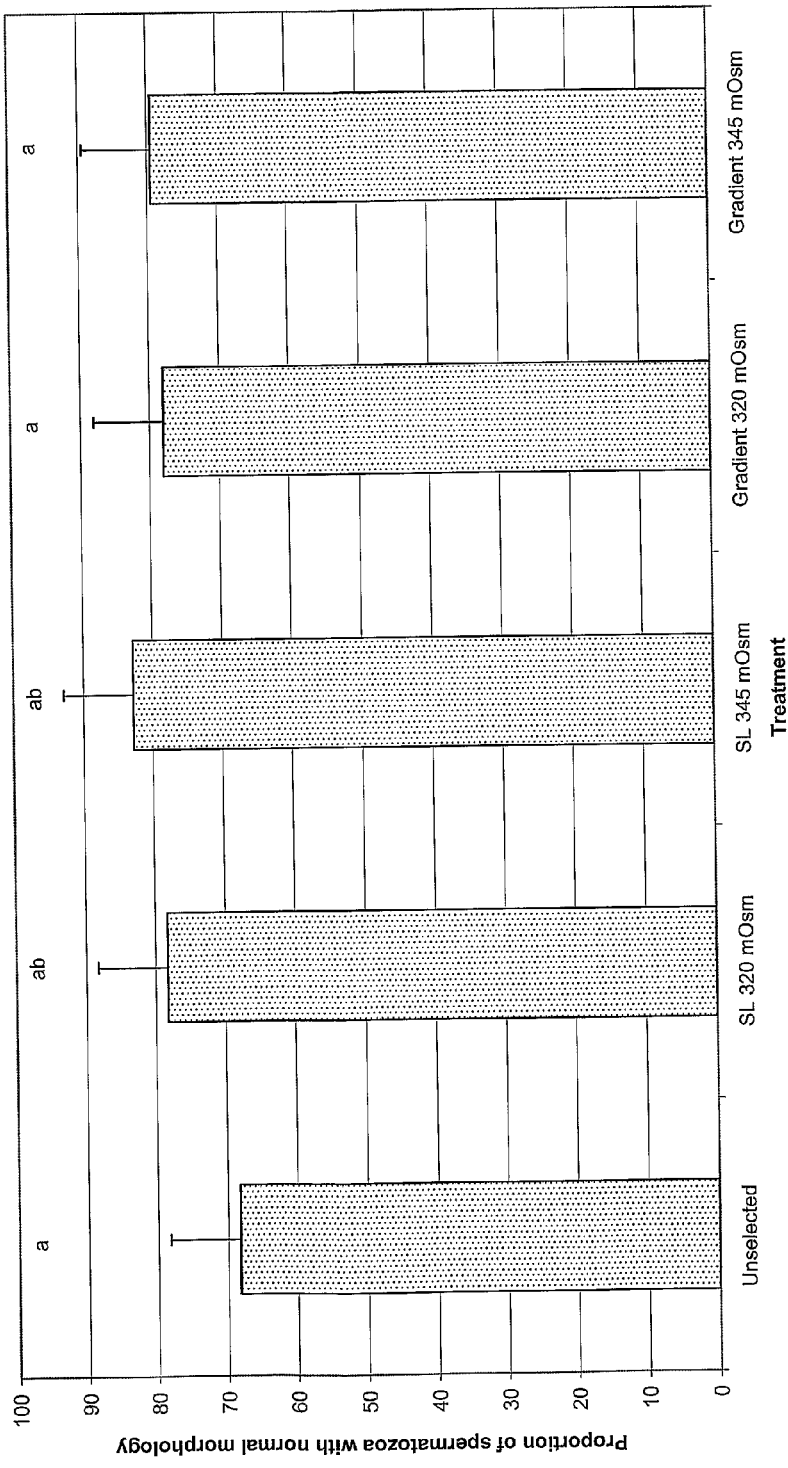
Figure 3: Effect of osmolarity of colloid on proportion of stallion spermatozoa with normal morphology after colloid centrifugation (n=15).

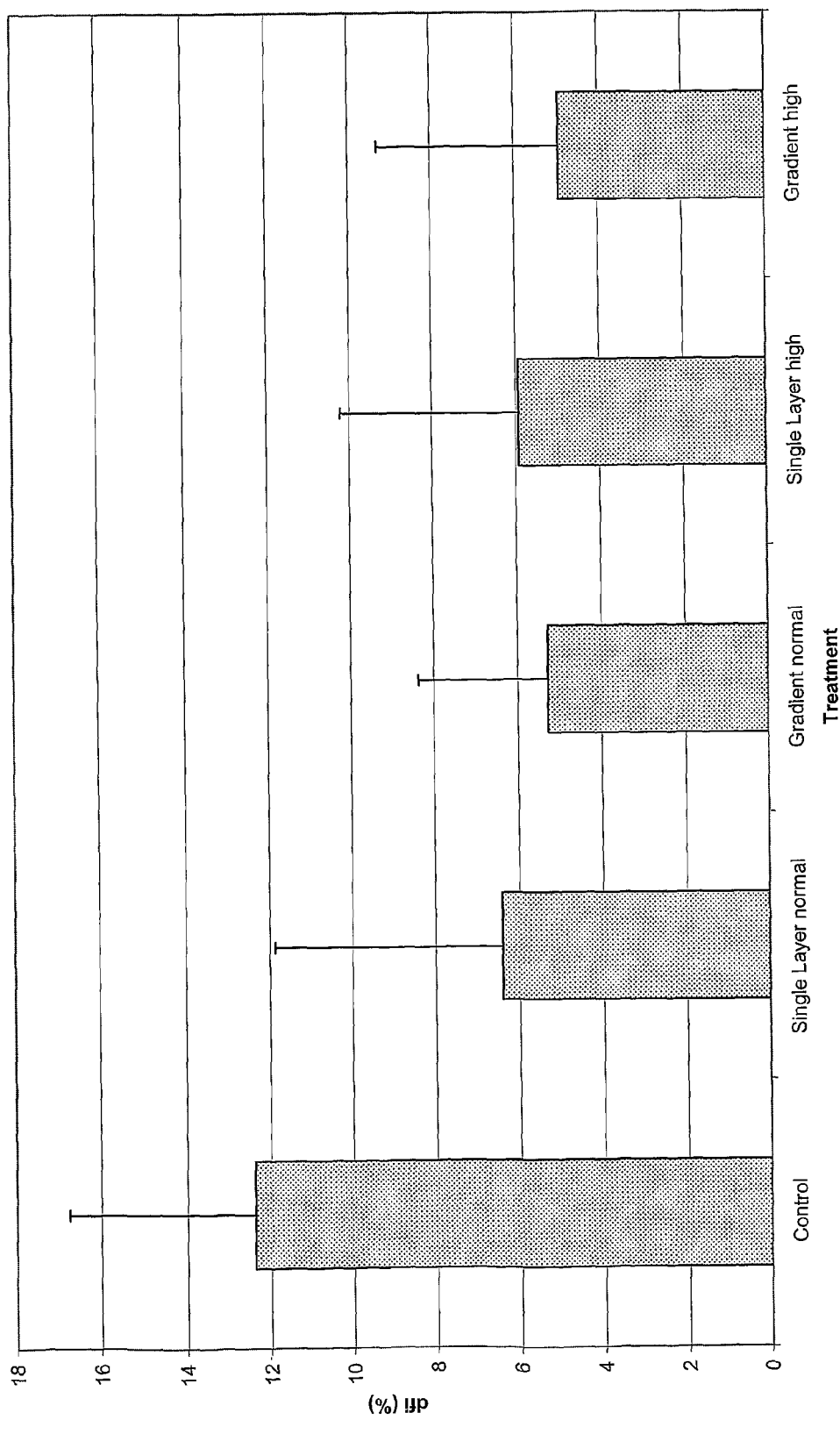
Figure 4: Effect of colloid osmolarity on sperm chromatin defects (n=12).

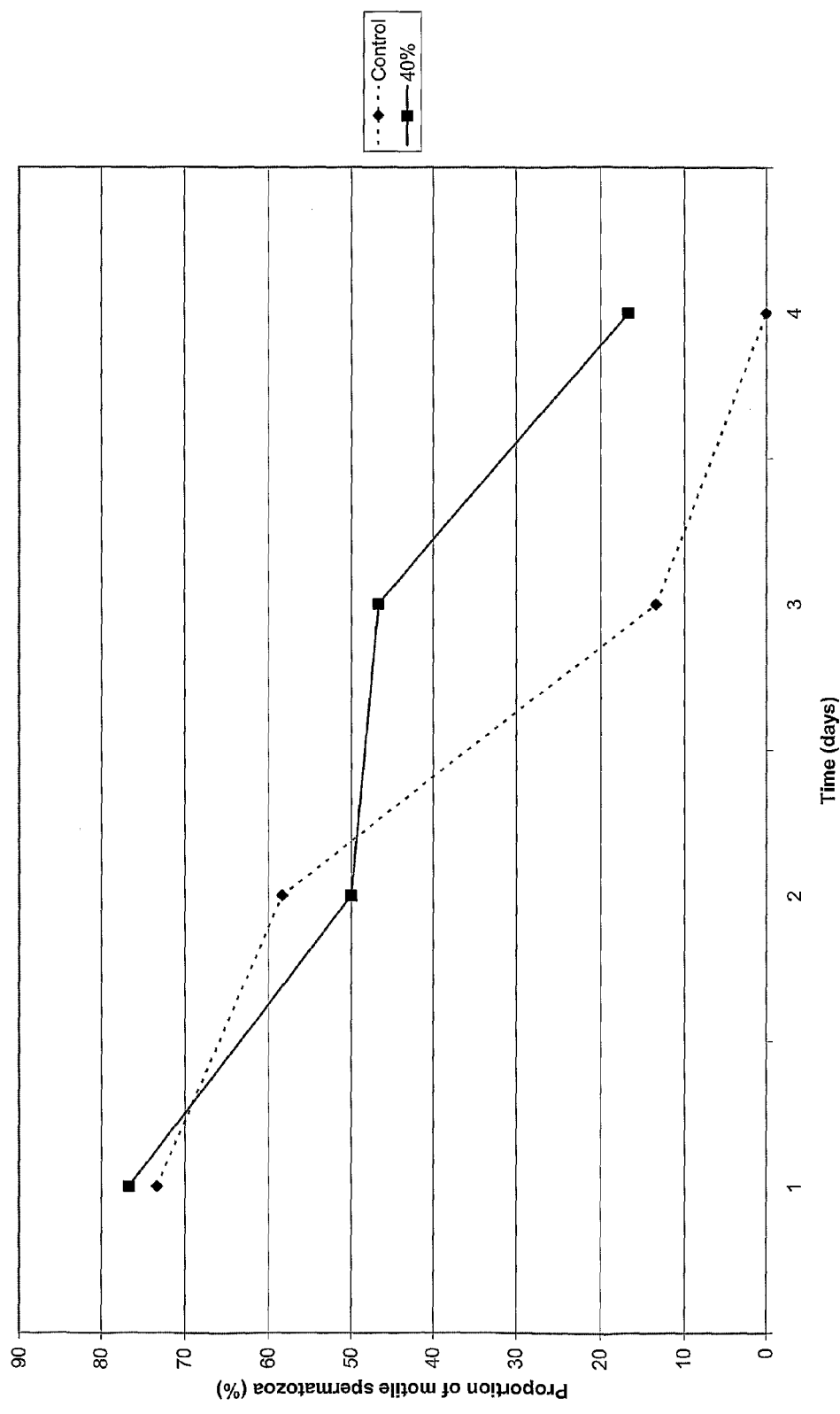
Figure 5: effect of separating spermatozoa from seminal plasma without concomitant selection for good quality spermatozoa using colloid density 40% (n=3).

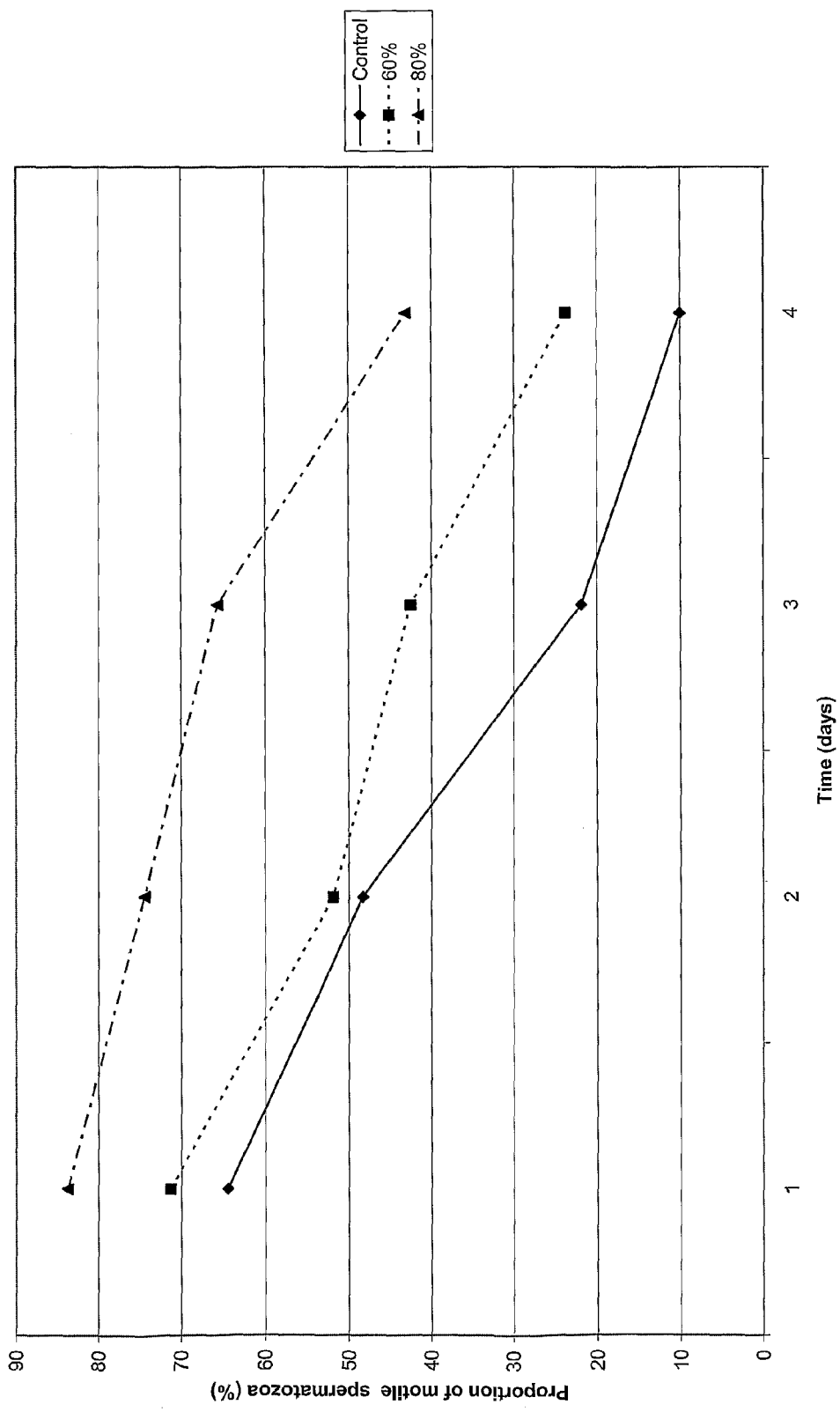
Figure 6: comparison of different densities of colloid (80% and 60%) used for single layer centrifugation (n=8).

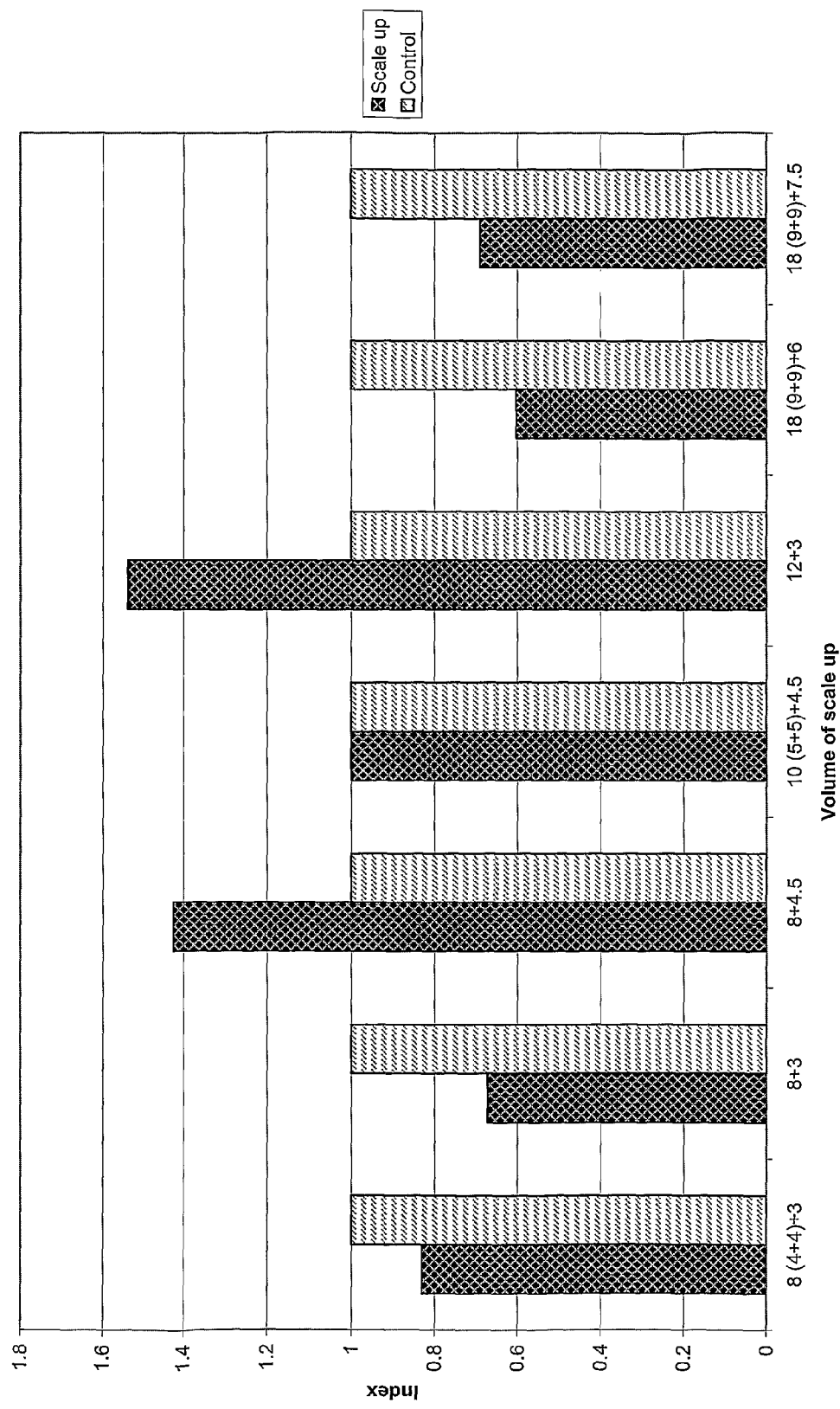
Figure 7: Effect of scaling-up single layer centrifugation on yield of stallion spermatozoa: control (4 mL colloid plus 1.5 mL extended ejaculate) indexed to 1 for each treatment.

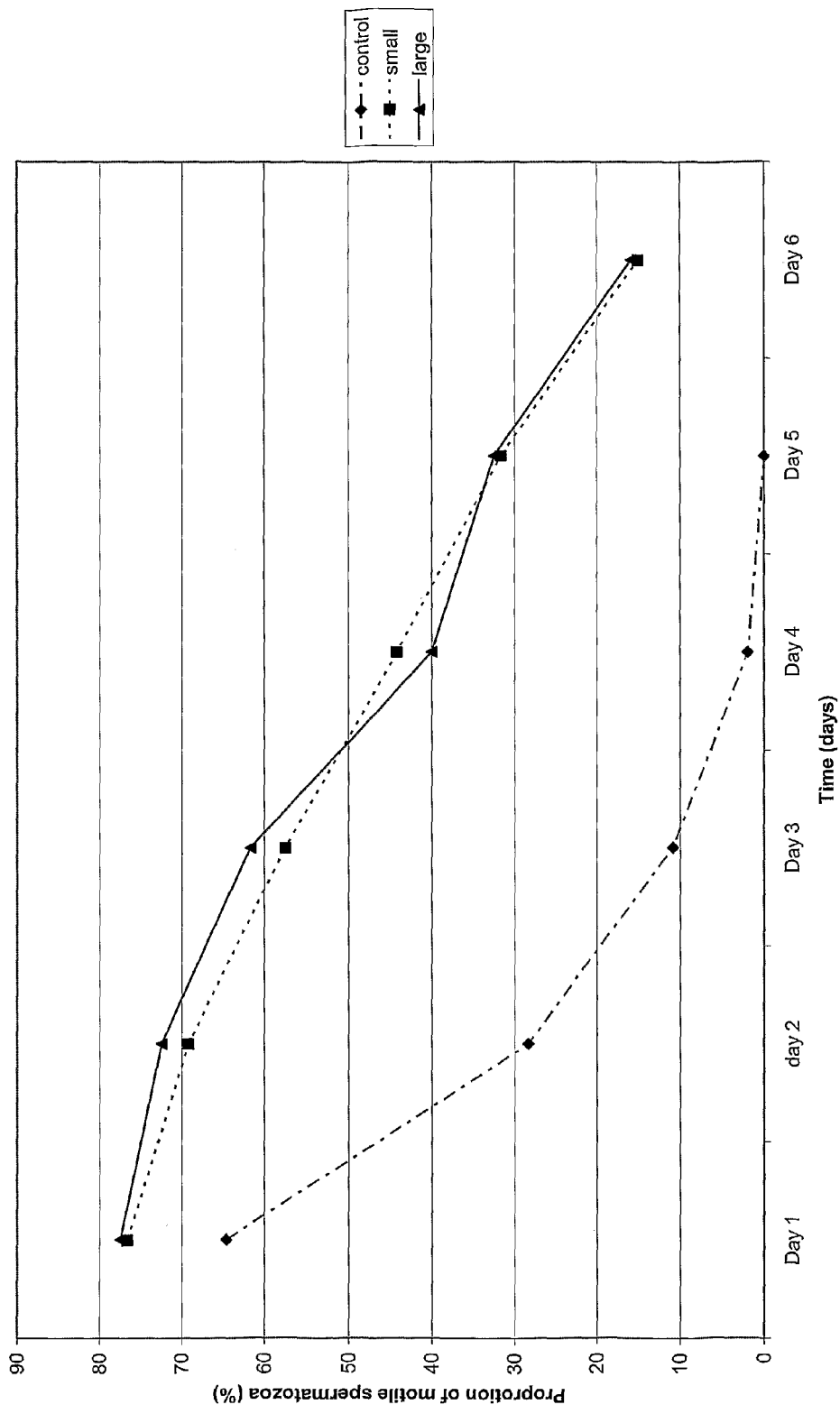
Figure 8: subjective motility in sperm samples before and after single layer centrifugation, comparing small (4.0 mL colloid plus 1.5 mL extended ejaculate) and large (20 mL colloid and 7.5 mL extended ejaculate.) treatments (n=8).

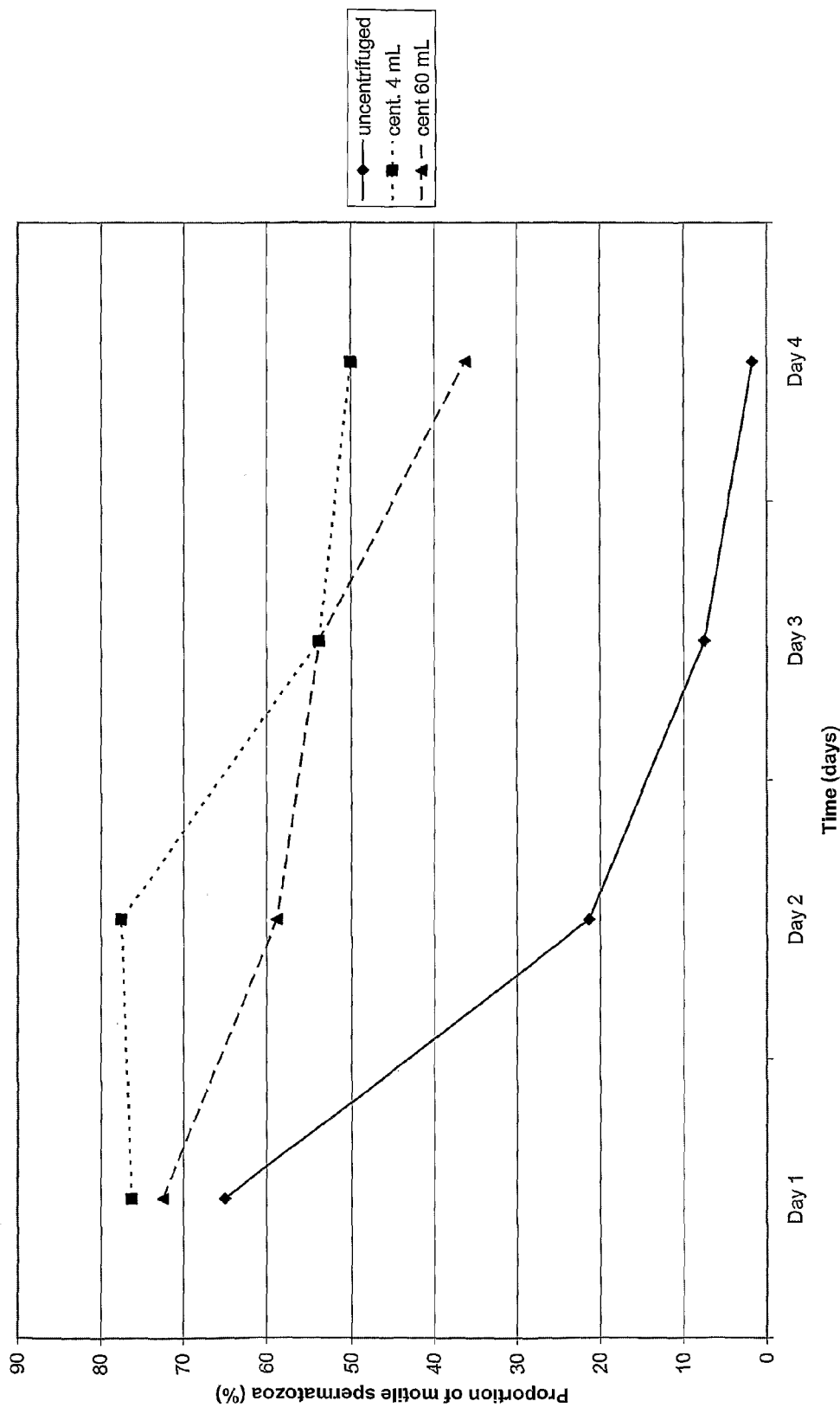
Figure 9: subjective motility in sperm samples before and after single layer centrifugation, comparing small (4.0 mL colloid plus 1.5 mL extended ejaculate) and extra-large (60 mL colloid and 22.5 mL extended ejaculate.) treatments (n=4).

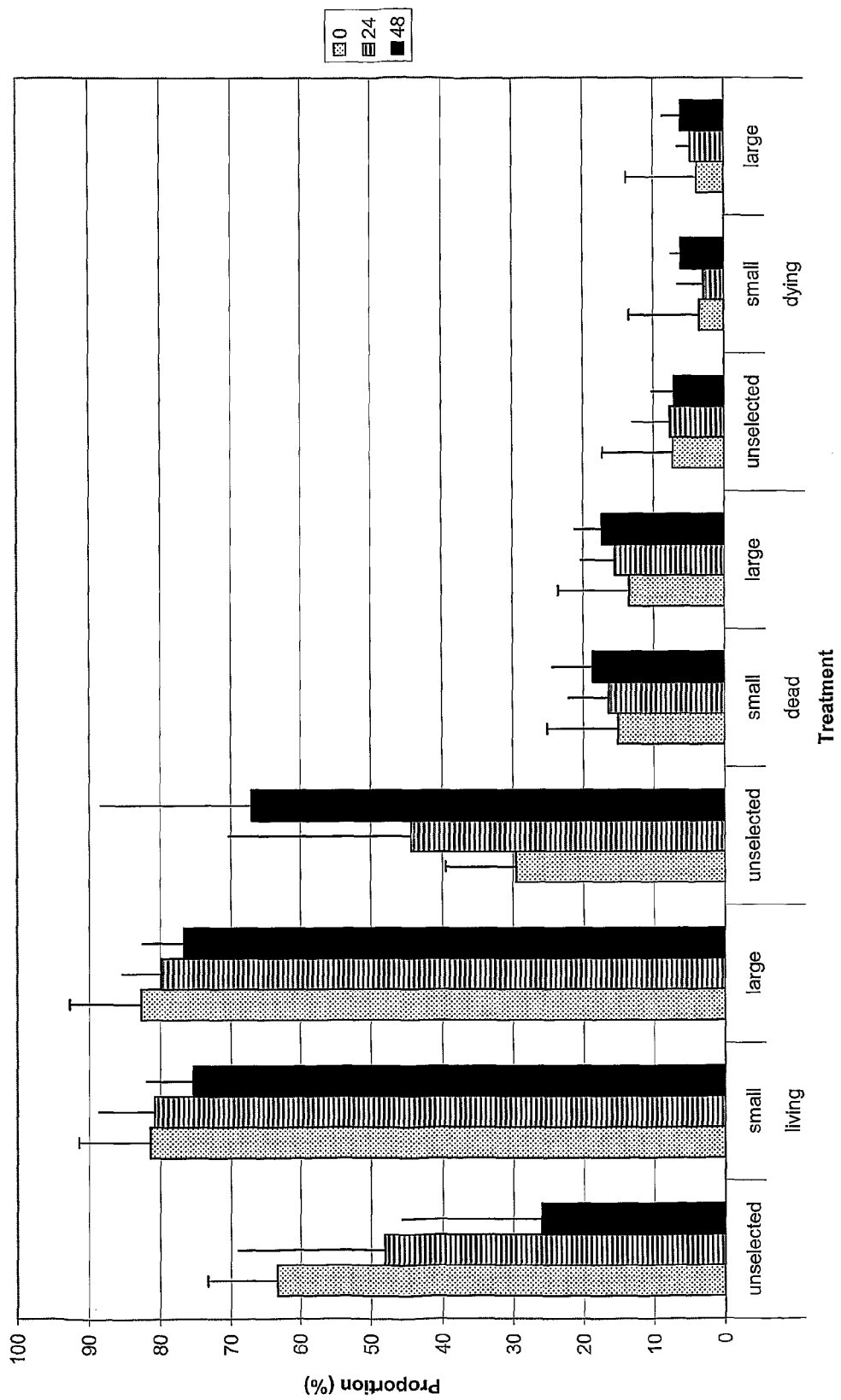
Figure 10: Effect of scaling-up the colloid centrifugation on stallion sperm viability (n=8).

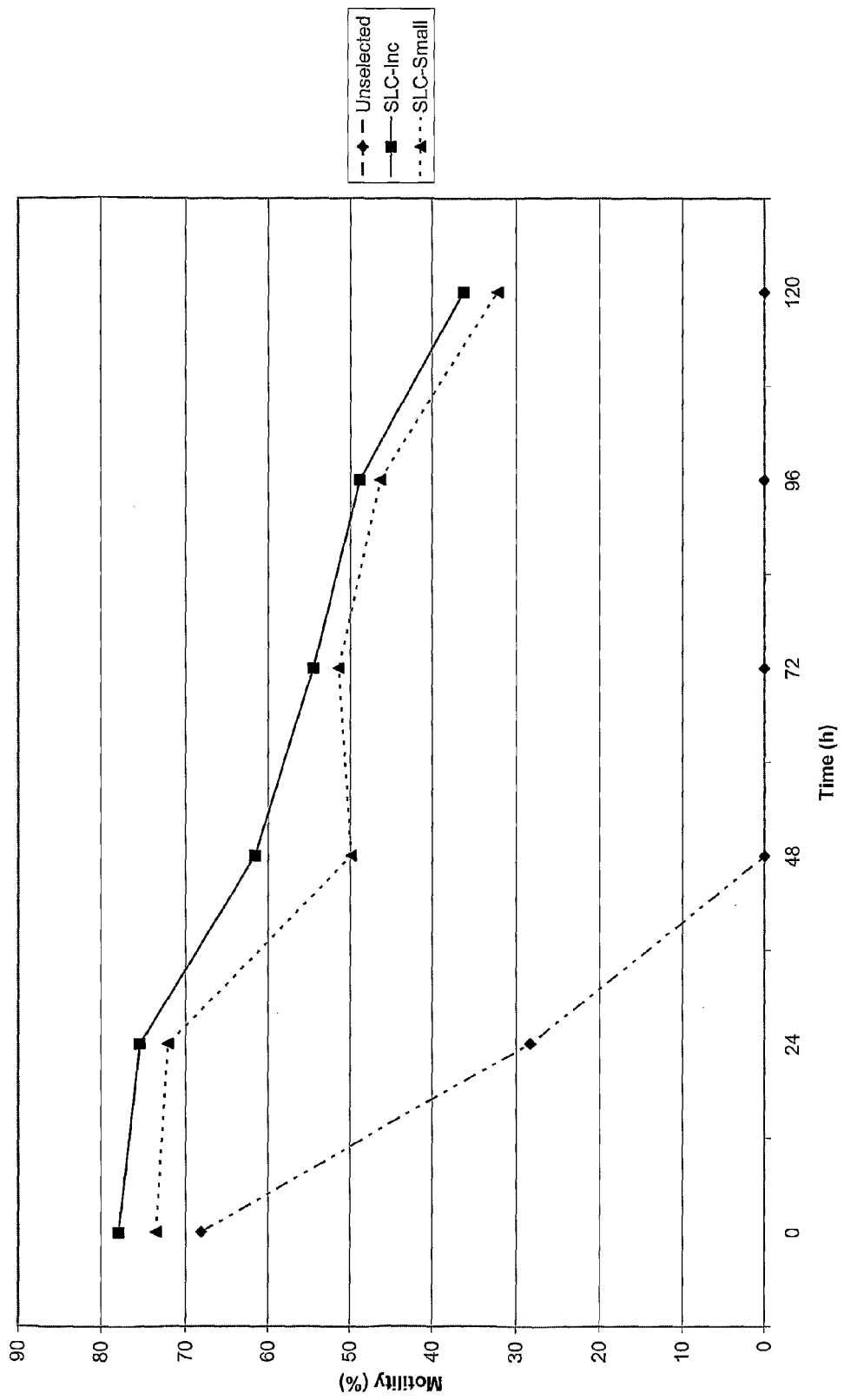
Figure 11: effect of scaling up colloid centrifugation on stallion sperm motility (n=7).

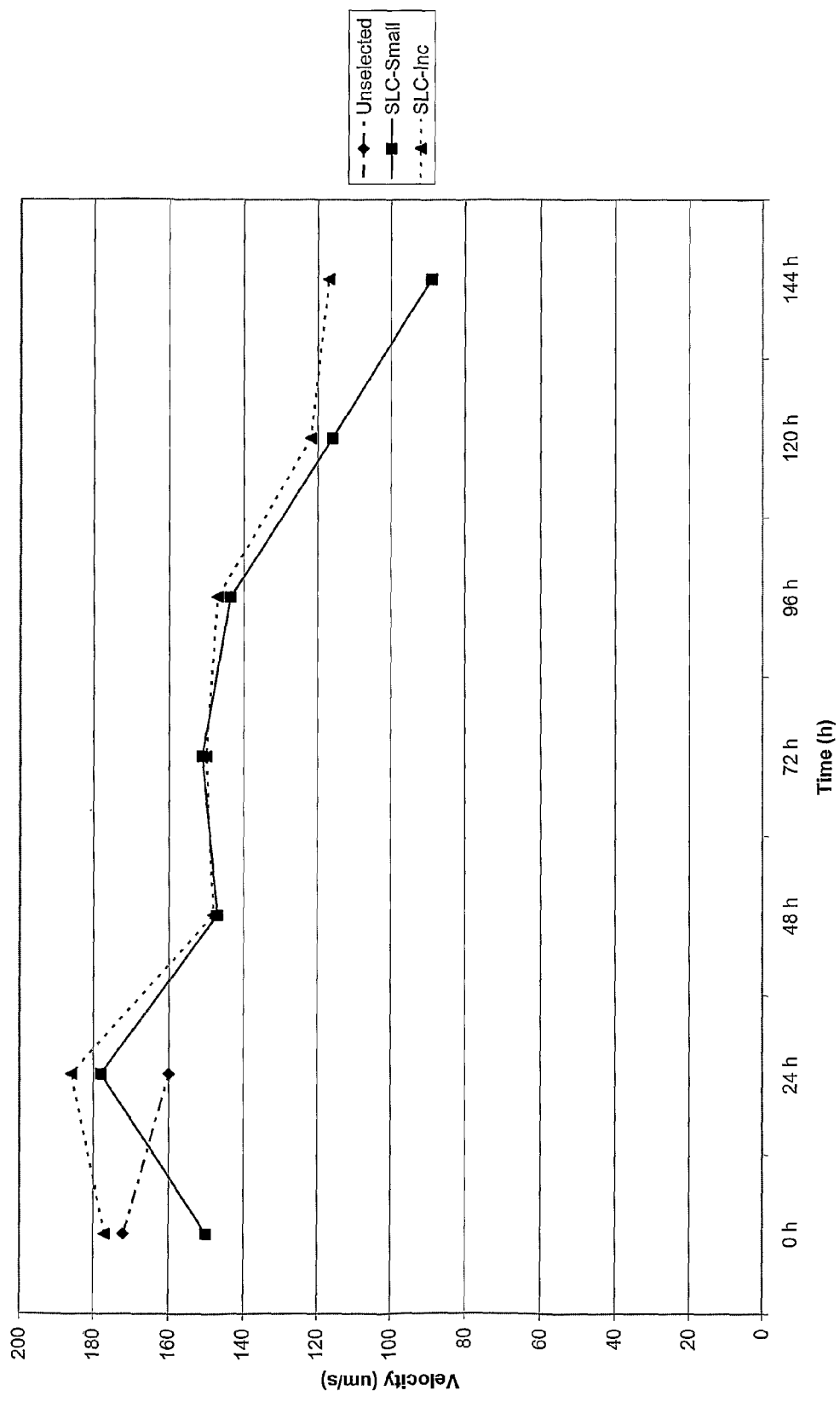
Figure 12: Effect of scaling-up colloid centrifugation on stallion sperm velocity (n=7).

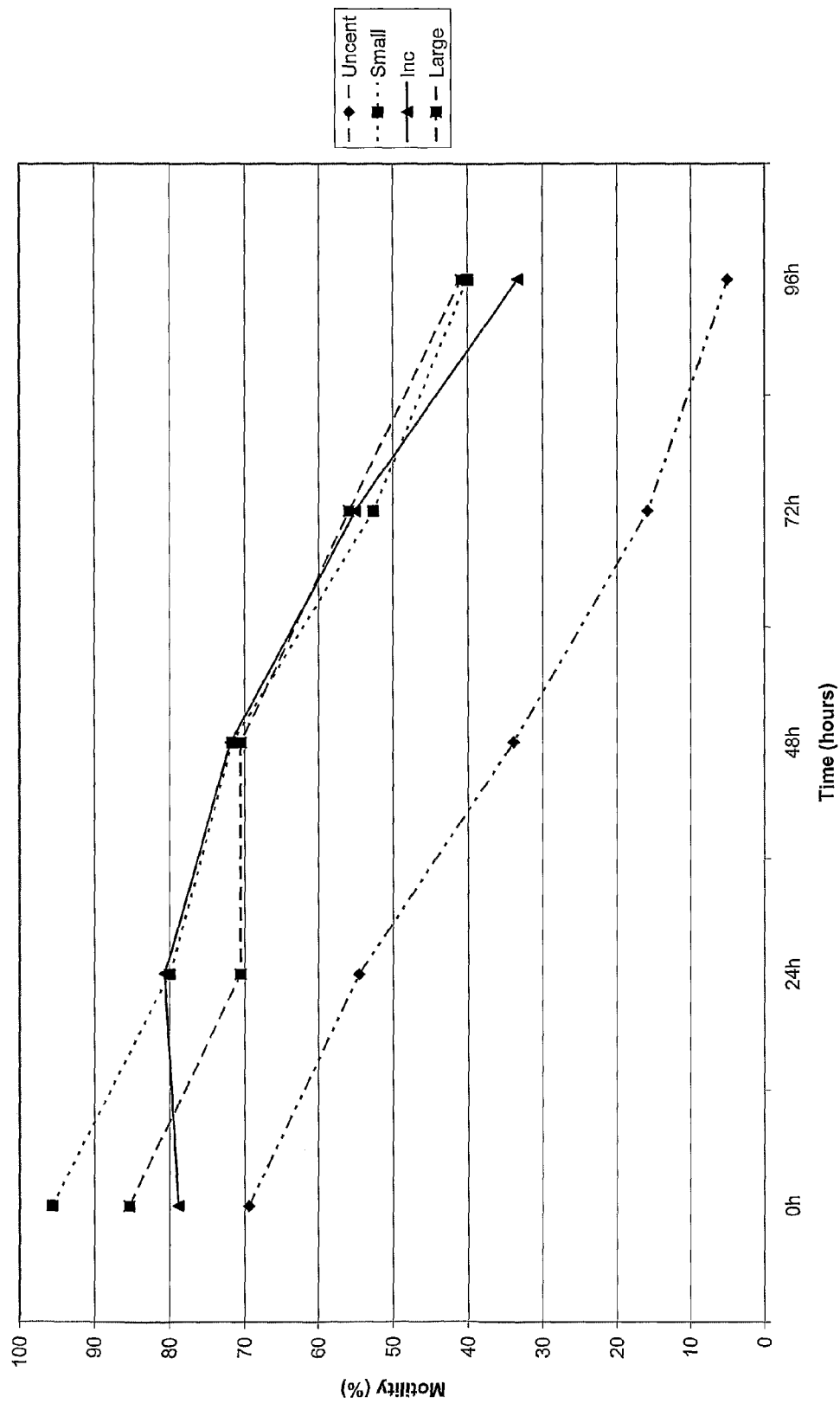
Figure 13: Effect of increasing both the volume of colloid and the volume of ejaculate on stallion sperm motility (n=9).

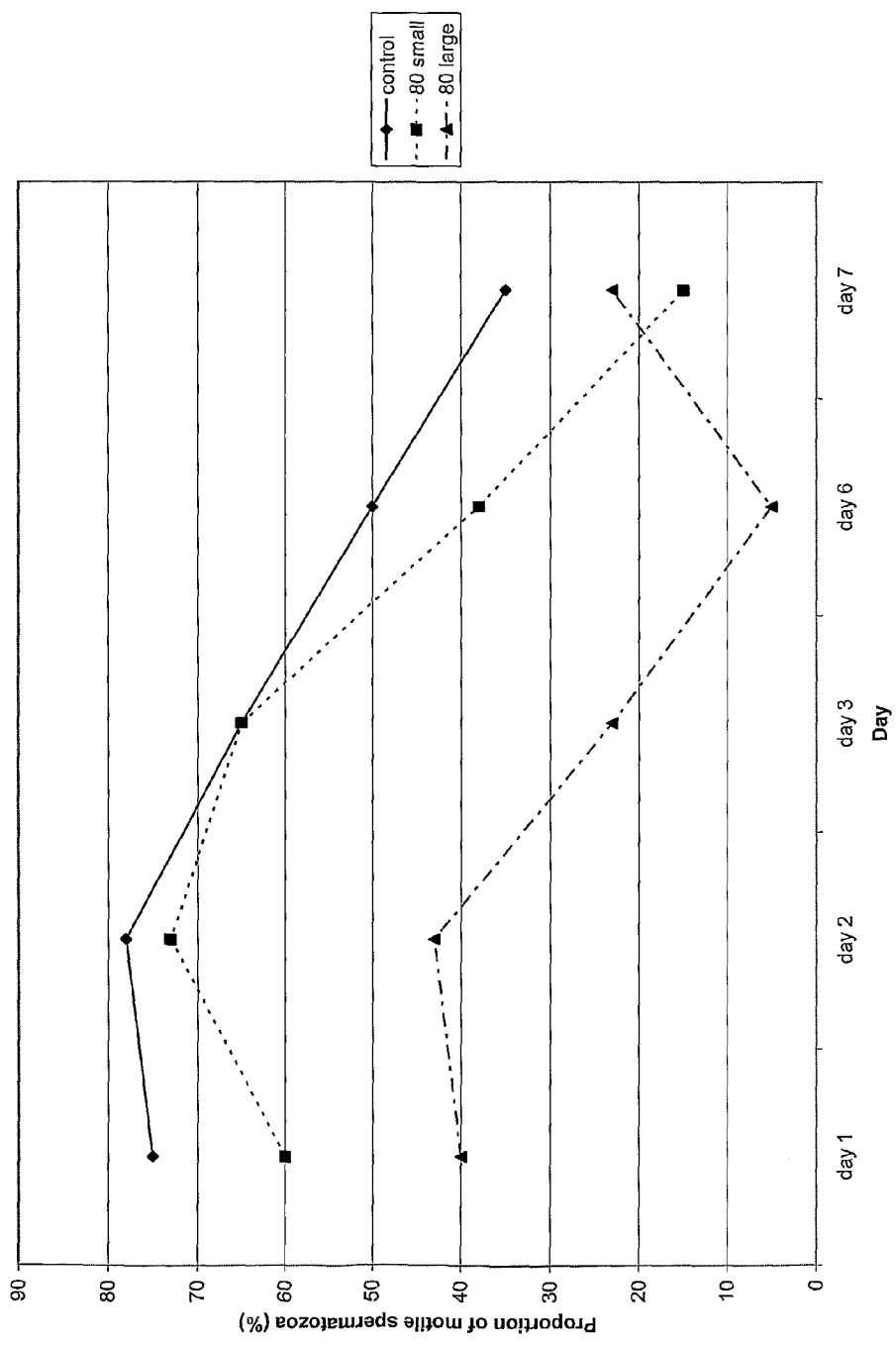
Figure 14: Effect of osmolarity of colloid on boar sperm motility after density gradient centrifugation in small and large centrifuge tubes: osmolarity 305 mOsm (n=4).
Note: Day 1 is day of preparation; day 2 is plus 24 hours etc.

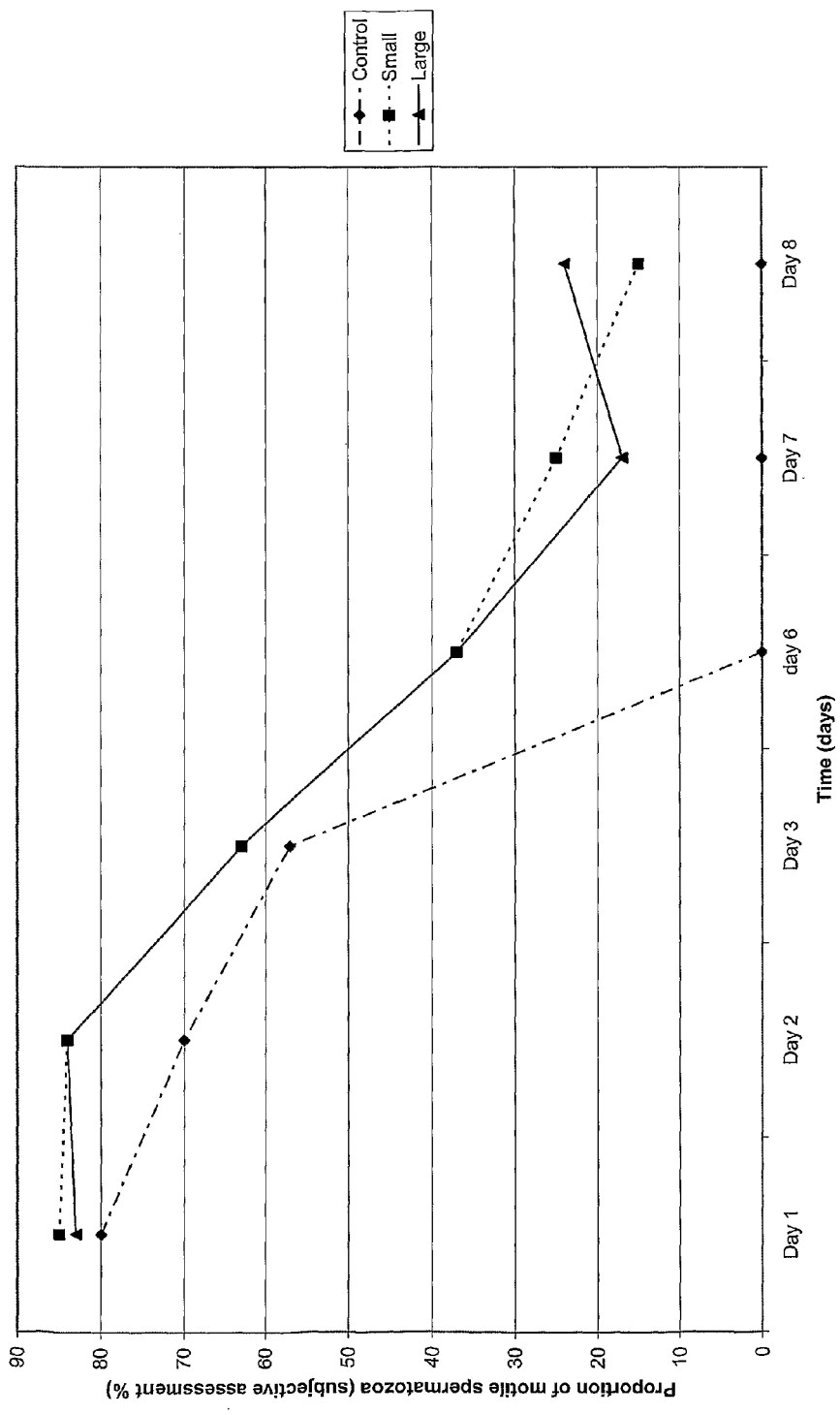
Figure 15: Effect of osmolarity of colloid on boar sperm motility after density gradient centrifugation in small and large centrifuge tubes: osmolarity 330 mOsm (n=8).
Note: Day 1 is day of preparation; day 2 is plus 24 hours etc.

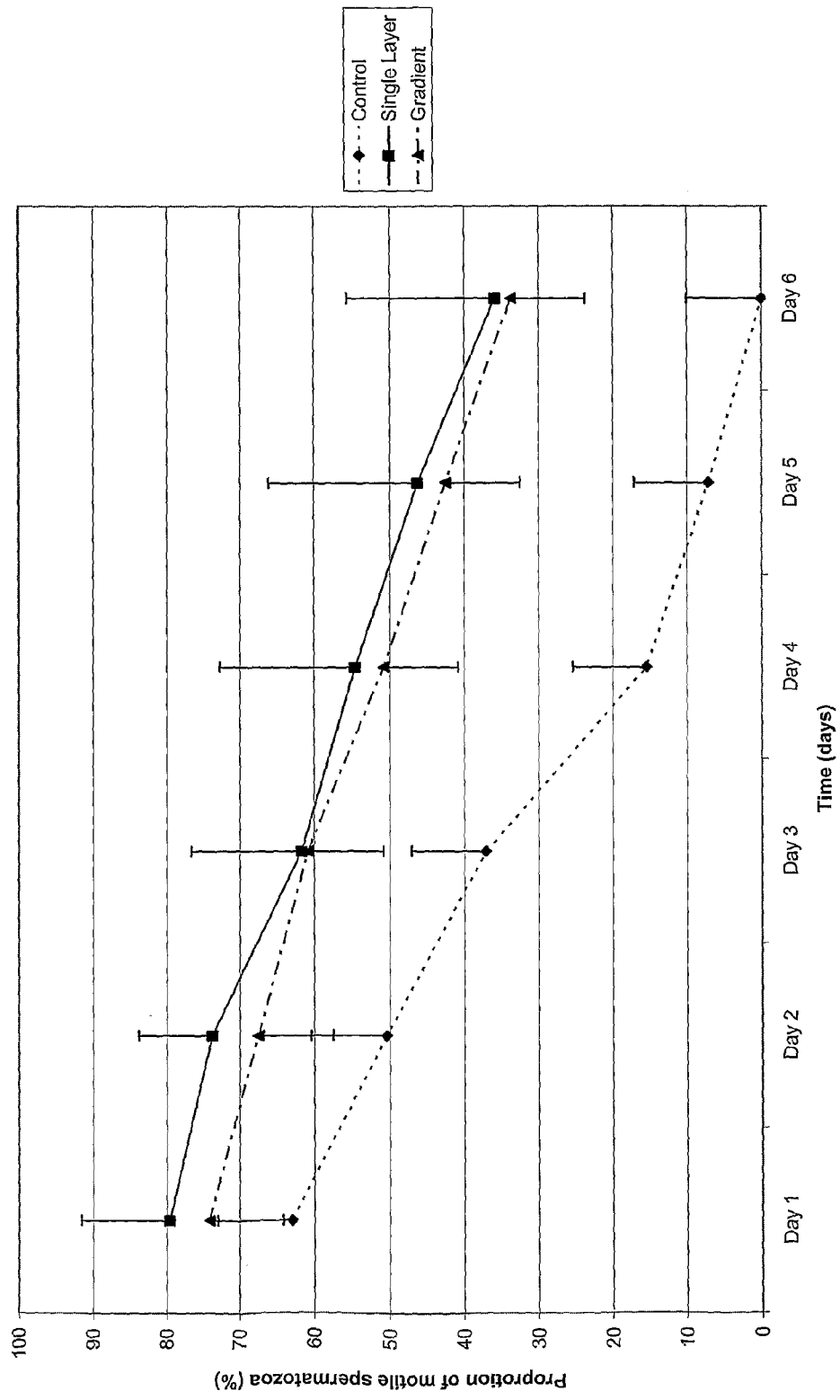
Figure 16: Comparison of density gradient centrifugation and single layer centrifugation of boar spermatozoa (n=12 ejaculates).
Note: Day 1 is day of preparation; day 2 is plus 24 hours etc

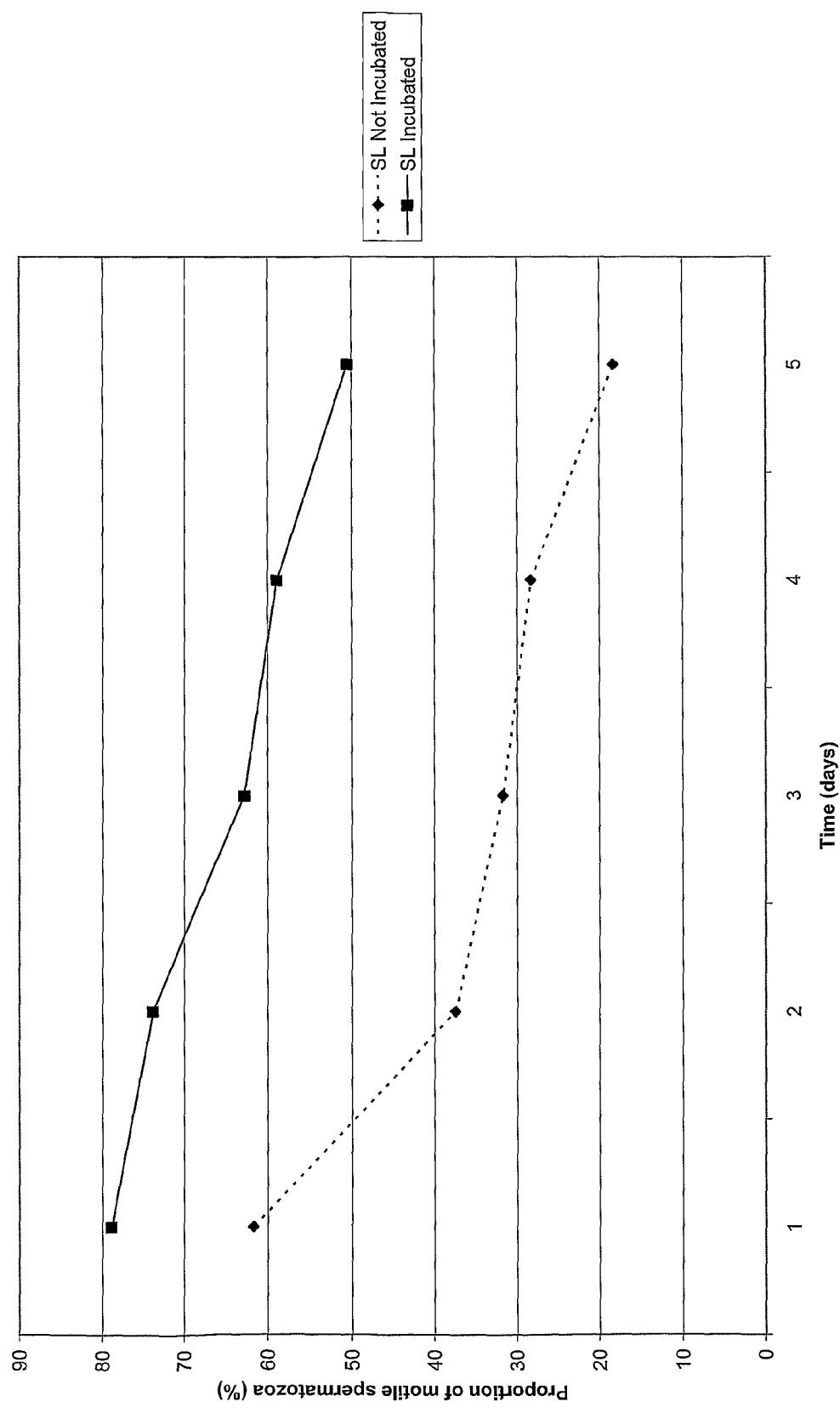
Figure 17: Effect of incubation at 37°C on the motility of boar spermatozoa from single layer preparations (n=18 ejaculates).

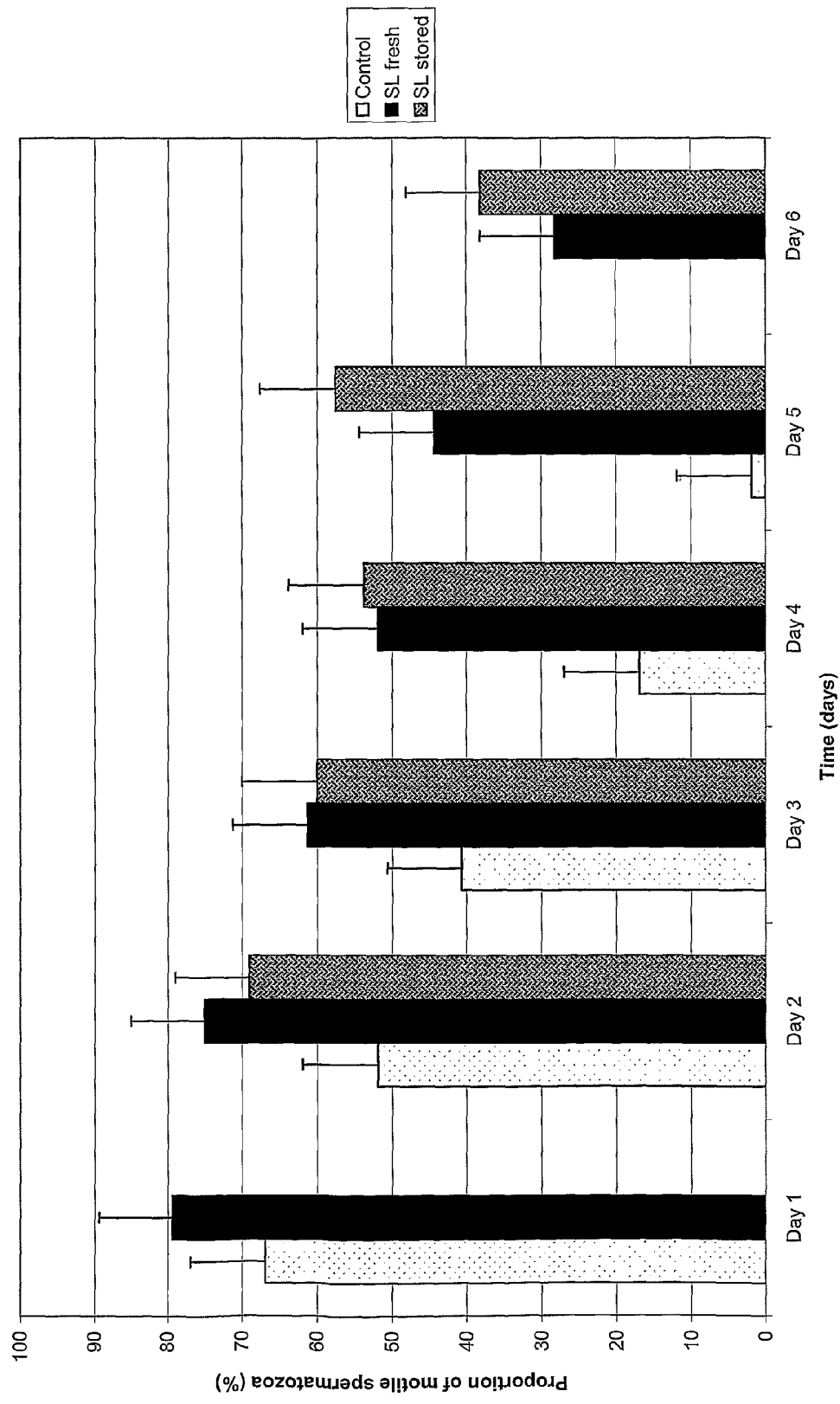
Figure 18: Comparison of colloidal centrifugation using fresh and stored boar spermatozoa (n=12 ejaculates).

COMPOSITION FOR SEPARATING SPERMATOZOA FROM A SEMEN SAMPLE

FIELD OF THE INVENTION

The present invention relates to the field of veterinary medicine, more specifically to compositions and methods useful for processing animal semen for use in assisted reproduction.

BACKGROUND OF THE INVENTION

Artificial insemination (AI) has been used in dairy cattle and pigs for several decades. However, methods of improving sperm quality in sperm doses used for AI are required for several reasons: (i) to remove spermatozoa from inhibiting factors in seminal plasma, e.g. decapacitating factors; (ii) to select the mature, normal and viable spermatozoa from the entire sperm population in the ejaculate; (iii) to separate spermatozoa from sources of reactive oxygen species which are detrimental to sperm survival. These functions are normally carried out by the female reproductive tract during natural mating but may be partly lacking when spermatozoa are artificially inseminated. Furthermore, when spermatozoa are to be used for in vitro fertilisation, these selection mechanisms are completely absent and the spermatozoa must be separated from the seminal plasma prior to use.

Artificial insemination (AI) has been used in dairy cattle and pigs for several decades. However, methods of improving sperm quality in sperm doses used for AI are required for several reasons: (i) to remove spermatozoa from inhibiting factors in seminal plasma, e.g. decapacitating factors; (ii) to select the mature, normal and viable spermatozoa from the entire sperm population in the ejaculate; (iii) to separate spermatozoa from sources of reactive oxygen species which are detrimental to sperm survival. These functions are normally carried out by the female reproductive tract during natural mating but may be partly lacking when spermatozoa are artificially inseminated. Furthermore, when spermatozoa are to be used for in vitro fertilisation, these selection mechanisms are completely absent and the spermatozoa must be separated from the seminal plasma prior to use.

Over the last 15 years, the technique of density gradient centrifugation has been used to prepare human spermatozoa for use in assisted reproduction (WHO, 1999). Originally, silica particles coated with polyvinylpyrrolidone were used, but more recent formulations have used silane-coated silica particles in the density gradient.

The prepared sperm suspensions are used immediately for in vitro fertilization, intra-cytoplasmic sperm injection or intrauterine deposition.

Commercially available colloid formulations for preparing human spermatozoa e.g. Puresperm, (Nidacon International AB) for assisted reproduction have an osmolarity of 300-310 mOsm, according to the company website and promotional literature. Until now, the only commercially available density gradient products for animal spermatozoa quoted in the literature also have an osmolarity within the range 300-310 mOsm, eg. Equipure and Bovipure (both made by Nidacon International). Although Bovipure was reported to give good results when used to prepare bovine spermatozoa for IVF (4), the use of Equipure as a density gradient for stallion spermatozoa did not give the same beneficial effects on sperm quality (5) as have been reported for human spermatozoa (6).

Preparation of human semen samples is commonly performed in aliquots of 1.5 mL semen. Although preparation of animal semen in such small volumes is adequate for preparing spermatozoa for IVF or ICSI, much larger sperm numbers are needed for artificial insemination in animals. Consequently, there is a need for simple and convenient methods for preparation of spermatozoa from animal semen at the site of collection and in adequate amounts for use in artificial insemination. There is also a need for animal-specific compositions suitable for use in such methods.

SUMMARY OF THE INVENTION

In a first aspect, the present invention relates to a composition for separation of spermatozoa from a semen sample, comprising at least one salt of an alkali metal and/or an alkaline earth metal, EDTA, a zwitterion buffer, silane-coated silica particles and water, said composition having a pH of 7.0-7.35 and an osmolarity of 300-345 mOsm.

In one embodiment of this aspect, the composition comprises
- sodium chloride in a concentration of 97.5-140.0 mM
- potassium chloride in a concentration of 4.0-5.5 mM
- glucose in a concentration of 1.0-1.4 mM
- EDTA in a concentration of 0.10-0.14 mM
- HEPES in a concentration of 15.0-19.0 mM
- Tri-sodium citrate in a concentration of 4.8-8.3 mM
- lactate in a concentration of 0-4.0 mM; and
- silane-coated silica particles in a concentration of 300-1000 g/l.

In a further embodiment of this aspect, the composition has a pH in the range 7.10-7.25, preferably about 7.15, before autoclaving. The composition further preferably has an osmolarity of 320-345 mOsm, such as 320-330 mOsm. The mean diameter of the silane-coated silica particles may be 10-1000 nm, preferably 10-100 nm.

In a further aspect, the invention relates to a method for preparing spermatozoa from a semen sample from a non-human animal, comprising the step of separating the spermatozoa from other semen constituents by centrifugation through a single layer of a colloid formulation.

In one embodiment of this aspect, the method makes use of the composition according to the first aspect.

In one embodiment of this aspect, the density of the colloid formulation is in the range of 1.05-1.14 g/ml, such as 1.051-1.11 g/ml. The formulation may have a pH of 6.8-7.4, preferably 7.0-7.3 and an osmolarity of 300-345 mOsm, such as 320-330 mOsm.

In one embodiment of this aspect, the method is performed in a non-plastic container, such as a glass container.

In one embodiment of this aspect, the method is performed in containers with volume of 10 ml or above 10 ml, such as 50-200 ml. The height of colloid formulation in the container may be 30-45 mm.

In one embodiment of this aspect, the whole ejaculate is processed.

In one embodiment of this aspect, the animal is a bird or a mammal, such as a horse, bull, pig or dog.

In one embodiment of this aspect, the mean diameter of the silane-coated silica particles is 10-1000 nm, preferably 10-100 nm.

In one embodiment of this aspect, the semen sample is not oligospermic.

In one embodiment of this aspect, spermatozoa are separated from seminal plasma and the cellular and non-cellullar components of seminal plasma, such as bacteria, viruses, leucocytes, particles etc. Each separated component may be used separately.

In one embodiment of this aspect, the method is used for prolonging the duration of sperm motility. This is further described in the examples below.

In one embodiment of this aspect, the method is used for reducing variation in sperm quality between ejaculates. This is further described in the examples below.

The different embodiments of the method according to this aspect may be combined with each other.

In a further aspect, the invention relates to a method for separating a sperm sub-population of interest from a semen sample from a non-human animal, comprising the steps providing a density gradient comprising at least two layers of the composition according to the first aspect, each layer having a different density;

separating the sperm sub-populations in the semen sample by centrifugation through the density gradient; and selecting the sperm sub-population of interest.

The sperm sub-population may be e.g. haploid spermatozoa or spermatozoa having normal motility, of e.g. equine, bovine or porcine origin.

Finally, the invention relates to spermatozoa prepared with the method according to the invention and to the use of such spermatozoa in AI, IVF and ICSI.

BRIEF DESCRIPTION OF THE DRAWINGS

FIG. 1: Effect on stallion sperm survival of using fresh or stored sperm for colloidal centrifugation (n=12). Note: day of collection=Day 1; hence Day 2=24 hours, Day 3=48 hours etc.

FIG. 2: Effect of washing (n=38) or not washing (n=38) the sperm pellet after single layer centrifugation on mean subjective motility estimates (%).

FIG. 3: Effect of osmolarity of colloids on stallion spermatozoa with normal morphology after colloid centrifugation (n=15).

FIG. 4: Effect of colloid osmolarity on sperm chromatin defects (n=12).

FIG. 5: Effect of separating spermatozoa from seminal plasma without concomitant selection for good quality spermatozoa using colloid density (n=3).

FIG. 6: Comparison of different densities of colloid (80% and 60%) used for single layer centrifugation (n=8).

FIG. 7: Effect of scaling-up single layer centrifugation on yield of stallion spermatozoa: control (4 mL colloid plus 1.5 mL extended ejaculate) indexed to 1 for each treatment.

FIG. 8: Subjective motility in sperm samples before and after single layer centrifugation, comparing small (4.0 mL colloid plus 1.5 mL extended ejaculate) and large (20 mL colloid and 7.5 mL extended ejaculate.) treatments (n=8).

FIG. 9: Subjective motility in sperm samples before and after single layer centrifugation, comparing small (4.0 mL colloid plus 1.5 mL extended ejaculate) and extra-large (60 mL colloid and 22.5 mL extended ejaculate.) treatments (n=4).

FIG. 10: Effect of scaling-up the colloid centrifugation on stallion sperm viability (n=8).

FIG. 11: Effect of scaling up colloid centrifugation on stallion sperm motility (n=7).

FIG. 12: Effect of scaling-up colloid centrifugation on stallion sperm velocity (n=7).

FIG. 13: Effect of increasing both the volume of colloid and the volume of ejaculate on stallion sperm motility (n=9).

FIG. 14: Effect of osmolarity of colloid on boar sperm motility after density gradient centrifugation in small and large centrifuge tubes: osmolarity 305 mOsm (n=4). Note: Day 1 is day of preparation; day 2 is plus 24 hours etc.

FIG. 15: Effect of osmolarity of colloid on boar sperm motility after density gradient centrifugation in small and large centrifuge tubes: osmolarity 330 mOsm (n=8). Note: Day 1 is day of preparation; day 2 is plus 24 hours etc.

FIG. 16: Comparison of density gradient centrifugation and single layer centrifugation of boar spermatozoa (n=12 ejaculates). Note: Day 1 is day of preparation; day 2 is plus 24 hours etc.

FIG. 17: Effect of incubation at 37° C. on the motility of boar spermatozoa from single layer preparations (n=18 ejaculates).

FIG. 18: Comparison of colloidal centrifugation using fresh and stored boar spermatozoa (n=12 ejaculates).

DETAILED DESCRIPTION OF THE INVENTION

The present invention aims to improve the prior art compositions and methods for preparation of spermatozoa from animal ejaculates with regard to the quality of, and also to the simplicity of, preparation. The improvement in sperm quality includes prolongation of sperm survival, improved sperm motility, viability, morphology, chromatin integrity and fertilizing ability. The improvements of the methods include increased yield and ease of operation, ability to process large volumes of ejaculate, selection of sperm sub-populations and optimization for individual species. This is further detailed in the examples.

The composition according to the invention may be produced as a stock composition. This stock composition has a density of approximately 1.14 g/ml. This stock composition may be used undiluted in certain applications but may also be diluted with a suitable buffer. Suitable dilutions are e.g. 80%, 70%, 67.5%, 65%, 60% and 40% of the stock composition. These diluted compositions may of course also be prepared directly, without first producing a stock composition.

The silane-coated silica particles used can be a commercially available product, such as RediGrad available from GE Healthcare, or any other particle composition with comparable characteristics.

Some examples of compositions according to the invention are given as Stock A (suitable for use with porcine species) and Stock E (suitable for other species, such as equine, bovine or canine species) in Table I below. Buffer E and buffer A may be used for making the corresponding diluted compositions, but also other buffers may be used. Buffer A may, as an example, be substituted for Beltsville Thawing Solution (BTS) in dilution of Stock A. The pH of the exemplified stock compositions is about 7.15, but this rises during autoclaving to about 7.33.

TABLE I

| Chemical | Stock E mM | Stock A mM | Buffer E mM | Buffer A mM | 80% E mM | 80% A mM |
|---|---|---|---|---|---|---|
| NaCl | 104 | 113 | 135 | 121 | 115 | 113 |
| KCl | 4.3 | 4.7 | 5.5 | 5.0 | 4.7 | 4.7 |
| Glucose | 1.1 | 1.2 | 1.2 | 1.3 | 1.2 | 1.2 |
| EDTA | 0.11 | 0.13 | 0.13 | 0.12 | 0.13 | 0.13 |
| HEPES | 16 | 18 | 18 | 19 | 18 | 18 |
| $CaCl_2$ | 2.5 | 2.7 | 0 | 0 | 0 | 2.7 |
| Na citrate | | | 7.6 | 8.1 | 5.8 | 1.6 |
| Ca lactate | | | 3.0 | | 2.5 | 0 |
| Na lactate | | | | 19 | | 3.8 |
| $H_2O$* | | | 1 L | 1 L | 0.2 L | 0.2 L |
| RediGrad | 1 L | 1 L | | | 0.8 L | 0.8 L |
| Density | 1.13 ± 0.005 g/ml | | | | | |
| mOsm | 320 | 330 | 320 | 330 | 320 | 330 |
| pH | 7.15-7.35 | 7.15-7.35 | | | 7.15 | 7.15 |

*water-for-injection quality

A method is needed to prolong the useable life of stallion spermatozoa destined for AI. The present inventors compared density gradient centrifugation or centrifugation through a single layer of colloid as potential methods of preparing stallion spermatozoa. Both methods appeared to prolong the duration of sperm motility compared to uncentrifuged spermatozoa (P<0.001), thereby potentially extending the useable life of treated stallion spermatozoa for AI. Furthermore, a comparison was made of the efficacy of selection using (i) freshly collected extended stallion semen, and (ii) semen samples stored overnight at 4° C. prior to the procedures.

For fresh, extended semen, a similar recovery yield of motile spermatozoa was seen for the two methods of preparation (27.0±6.56 million spermatozoa versus 32.6±7.79 for single layers and density gradients, respectively]. However, the yield was reduced by 18-20% when cold-stored semen was used for centrifugation compared to fresh semen, and greater variation between ejaculates was observed than for fresh ejaculates. Again, sperm motility and sperm survival were improved in the centrifuged sperm preparations compared to stored, unprocessed ejaculates. It is concluded that the two colloid centrifugation techniques produce equivalent sperm preparations, and that the single layer method would be convenient for use in the field. This is further described in example 1.

Sperm morphology and chromatin integrity have been linked to the fertility of stallion spermatozoa. Previous studies with human ejaculates have shown that the proportion of spermatozoa with normal morphology and with intact chromatin can be increased by using density gradient centrifugation (6). The present inventors investigated whether such methodology could be effective for stallion semen, by using either density gradient centrifugation or the above mentioned new method, single layer centrifugation. There was a significant increase in the proportion of morphologically normal spermatozoa in the sperm preparations after colloidal centrifugation regardless of which centrifugation method was used (before centrifugation 67.5±13.06%; after single layer 77.1±9.3%; after density gradient 76.7±8.7%; P<0.001). Moreover, the variation between stallions was reduced considerably by centrifugation. Some of the morphological abnormalities were considerably reduced after colloidal centrifugation, e.g. the incidence of proximal cytoplasmic droplets decreased by 20% and the incidence of distal cytoplasmic droplets by 50%, whereas colloidal centrifugation had little impact on the proportions of narrow or pear-shaped heads present. Overall, these results suggest that colloidal centrifugation is a suitable method for harvesting spermatozoa with normal morphology from ejaculates to be used for AI and, furthermore, may reduce some of the variation seen between stallions. This is further described in example 1.

In addition, both methods of colloidal centrifugation yielded sperm preparations in which chromatin integrity was significantly improved (DNA fragmentation index in unselected preparations, 11.0±4.6; single layer centrifugation, 4.8±2.6; density gradient centrifugation, 4.8±2.8; P<0.001). There was no difference between the two centrifugation methods. Furthermore, there were negative relationships between normal morphology and the DNA fragmentation index (DFI) (P<0.001), normal morphology and the standard deviation of DFI (SD_DFI), (P<0.001), and DFI and pregnancy rate (P<0.03). For specific defects, there was a direct relationship between the incidence of pear shaped heads and DFI (P<0.05), nuclear pouches and DFI (P<0.001), and midpiece defect and DFI (P<0.01); between detached heads and SD_DFI (P<0.001), and between detached heads and mean_ DFI (P<0.05). In conclusion, single layer centrifugation was as effective as density gradient centrifugation in enriching stallion sperm preparations for spermatozoa with normal chromatin structure and thus may help to improve pregnancy rates for artificial insemination. The presence of certain morphological defects may be indicative of chromatin damage and could be used as a marker for predicting the fertility of insemination doses. This is further described in example 1.

The use of colloid centrifugation to prepare animal spermatozoa for AI will depend on processing large volumes of ejaculate or large numbers of spermatozoa. Methods to increase the volume of ejaculate which can be handled and to reduce loss during centrifugation were investigated by altering parameters such as the osmolarity and density of the colloid formulation and the use of centrifuge tubes of different materials (glass versus plastic) and sizes (10 vs. 50 mL). Reducing the density of the colloid used for the single layer substantially increased the yield of motile spermatozoa compared to the normal density colloid (mean±SD: 72.6±28.9 million compared to 28.9±24.7 million), while also prolonging sperm survival by 24 hours compared to the uncentrifuged ejaculate. Using glass instead of plastic tubes significantly increased the mean yield: (42.2±22.14 million and 39.3±19.87 million spermatozoa for glass and plastic respectively; P<0.01). Use of large centrifuge tubes (50 mL) together with increased volumes of colloid and semen ("scale-up") produced variable results, probably due to inter-ejaculate differences. However, volumes of 8-10 mL colloid (either in one or two layers) together with 4.5 mL extended semen in 50 mL tubes, gave the highest yields compared to the usual volumes in 10 mL tubes, indicating that it should be possible to recover sufficient numbers of spermatozoa for AI. This is further described in example 3.

In a comparison of two osmolarities of colloid formulation, "normal" (320 mOsm) and "high" (345 mOsm), mean yields for single layers were 30.19 (±16.9) and 25.8 (±18.5) million spermatozoa respectively for the two osmolarities, whereas yields for density gradients were 31.84 (±19.7) and 26.46 (±20.0) million spermatozoa respectively, with considerable variation between ejaculates. These differences are not statistically significant. However, use of the high osmolarity colloid for the single layer resulted in an increase in the number of morphologically normal spermatozoa in the preparation (P<0.001). Furthermore, this trend was also observed for density gradients, although here the difference was not quite statistically significant (P<0.051). For individual morphological abnormalities, differences in the ability of the normal and high osmolarity colloid formulations to remove abnormal spermatozoa were not significant. Therefore, increasing the osmolarity of the colloid formulation may be beneficial for processing ejaculates containing a high proportion of abnormal spermatozoa. This is further described in example 3.

In a further example, the single layer method of colloidal centrifugation was modified to speed up the process and scaled-up to allow the whole ejaculate, which is voluminous in stallions, to be processed in a small number of large tubes. The omission of the second centrifugation "washing" step from the original protocol resulted in considerable time-saving and did not adversely affect sperm motility. For the scale-up, use of 8 to 12.5 mL colloid (80%) with 5 mL ejaculate did not give as good sperm motility in the sperm preparations as the 4 mL colloid in 10 mL centrifuge tubes. However, when either 15 or 20 mL colloid of various densities (60-80%) was used to centrifuge 7.5 mL extended ejaculate in 50 mL centrifuge tubes, sperm preparations were obtained which were considered to be equivalent in quality to those from normal-sized preparations. It was found that 15 ml 60% colloid gave the best sperm preparations in terms of sperm yield and sperm survival. Sperm motility was not different among treatments. In addition, the use of 60 mL colloid (80%) with 22.5 mL extended ejaculate in 200 mL centrifuge tubes gave sperm preparations which were considered to be similar in motility and length of survival to the sperm preparations from 4 mL colloid in 10 mL centrifuge tubes. Finally, the prepared spermatozoa were capable of fertilisation since pregnancies were achieved following insemination of the cooled, transported, centrifuged spermatozoa. This scale-up is further described in example 4.

The fertilising ability of selected frozen-thawed bovine spermatozoa was tested using in vitro fertilisation (IVF), the spermatozoa being prepared either on a density gradient or on a single layer of colloid. Mean fertilisation rate, blastocyst development rate and total number of cells were 56.3±23.3%, 23.5±17.4% and 83.2±29.9 respectively for density gradient-prepared spermatozoa, and 58.1±23.3%, 24.5±14.3% and 94.6±23.4 respectively, for spermatozoa prepared on a single layer of colloid. Mean values of various parameters of computerized analysis of sperm motility were not different between the two sperm preparation methods. These results confirm the reports for stallion and boar, namely that spermatozoa prepared on a single layer of colloid are not different in behaviour or properties to gradient-prepared spermatozoa, and further indicate that there is no difference in the fertilising abilities of sperm in the two types of preparations. This is further described in example 6.

Colloidal centrifugation has been used previously to select spermatozoa with normal morphology. Within the framework of the present invention, an attempt was made to select spermatozoa of normal size from a polymorphic population in a bull ejaculate. Single layers of colloid of different densities were used to identify suitable densities for the density gradient. Using colloid densities of 55% and 70%, it was possible to obtain two sperm sub-populations, one containing nearly all normally sized spermatozoa, and the other enriched for the macrocephalic spermatozoa. The microcephalic spermatozoa were selected out by the lowest density colloid and therefore did not appear in either of the selected sub-populations. This is further described in example 5.

Obstacles to the use of density gradient centrifugation in other species, such as the boar, are similar to those listed for the stallion. The present inventors investigated the following: (i) the effect of increasing the osmolarity of a colloid formulation on the efficacy of boar sperm selection during density gradient centrifugation, with a view to developing colloid formulations specific for animal spermatozoa, (ii) a comparison of density gradient centrifugation with centrifugation on a single layer of colloid for preparing boar spermatozoa, (iii) the effect on boar spermatozoa of autoclaving the colloid, and (iv) washing the spermatozoa after colloidal centrifugation.

The results showed that increasing the osmolarity of the colloid used for density gradient centrifugation of boar spermatozoa increased the proportion of motile spermatozoa in the resulting sperm preparation. Furthermore, sperm motility was retained for at least 24 hours longer in the centrifuged sperm preparations than in controls (uncentrifuged aliquots), that is, 7 or 8 days for spermatozoa centrifuged on a density gradient compared to less than 6 days for uncentrifuged spermatozoa. For the comparison of the single layer of colloid and density gradient, sperm motility was significantly better ($P<0.0.001$) in the centrifuged sperm preparations (means±sd: 79.6±8.1% and 74.2±12.0% for single layer and density gradient respectively) than in the uncentrifuged controls (62.9±12.7%). The mean yield of motile spermatozoa for the single layer was 67.5±25.6%, and for the density gradient was 59.6%±22.3% (ns). Survival was significantly increased by colloidal centrifugation (uncentrifuged preparations 3.1±0.3 days, SL 5.5±0.79 days, DG 5.75±0.62 days; $P<0.001$ for uncentrifuged versus centrifuged; SL vs DG ns). The presence of bacteria in the uncentrifuged sperm samples may have contributed to the demise of the spermatozoa. Colloidal centrifugation appeared to remove the bacteria.

Autoclaving the colloid formulation did not have an effect on sperm numbers, sperm motility or sperm survival, compared to not autoclaving the colloid. Furthermore, washing the sperm pellet obtained after colloidal centrifugation versus not washing the sperm pellet had no effect on sperm numbers, sperm motility or sperm survival. Boar spermatozoa could be stored for 24 hours before centrifugation without having a detrimental effect on sperm motility and duration of motility in the centrifuged preparations. In conclusion, increasing the osmolarity of the colloid formulation improves the selection of spermatozoa during density gradient centrifugation. In conclusion, centrifugation on a single layer of colloid produces sperm preparations which are similar in motility and yield to those from density gradients, and these preparations show improved sperm motility and duration of survival compared to control (uncentrifuged) sperm samples. The single layer method may facilitate development of a scaled-up method for preparing large volumes of ejaculate. This is further described in example 6.

The present inventors investigated the use of SLC to prepare dog spermatozoa for AI, comparing sperm motility and morphology in unselected and selected sperm samples. Mean sperm motility was increased from 77.2±19.6% before SLC to 87.6±2.7% after SLC while mean progressive motility was increased from 48.6±18% to 67.9±11%. Mean normal morphology was 62.2±42.8 in unselected samples and 82.5±19.1% in SLC-selected samples. After storage for 7 days at 4° C., sperm motility was <5% in unselected sperm samples and 57±11.3% in the SLC-selected sperm preparations. The sperm yield varied from 12-47% depending on the sperm quality in the original ejaculate. Conclusion: These preliminary results indicate that SLC may be a useful method for improving dog sperm quality in sperm doses for AI. This is further described in example 7.

EXAMPLES

The following examples further describe some specific embodiments of the invention. These examples should not be considered as limiting and the scope of the invention is that of the appended claims.

Example 1

Stallion

Objectives: (i) to compare single layer centrifugation (SLC) and density gradient centrifugation (DGC) on stallion sperm quality in terms of sperm motility, yield, sperm morphology and chromatin integrity, and survival (retention of motility) using freshly collected stallion semen; (ii) to compare sperm quality following colloid centrifugation of fresh and stored stallion semen.

Methods: semen was collected from 10 stallions at commercial AI studs using standard methods. The ejaculates were extended using home-made or commercially available semen extenders (Kenneys' extender [7], INRA 96 [IMV, France)) warmed to 37° C. and the sperm concentration was adjusted to ca. 100×10⁶/ml. Aliquots from 38 ejaculates were used for DGC and SLC as follows: a density gradient was prepared by pipetting 2 mL of 80% colloid E into a centrifuge tube and carefully layering 2 mL of the lower density layer on top; an aliquot (1.5 mL) of extended semen was pipetted on top of the upper layer of colloid. The gradient was centrifuged at 300×g for 20 minutes, after which the supernatant and most of the gradient material was discarded. The sperm pellet was transferred to a clean centrifuge tube containing 5 mL Kenney's extender and was washed by centrifuging for 10 minutes at 500×g. Following washing the sperm pellet was resuspended in fresh Kenney's extender (1 mL). For SLC, the method was similar to that for DGC with the exception that 4 mL of 80% colloid E were placed in the centrifuge tube instead of two layers of different densities (2 mL of each density).

Sperm quality in the unselected and centrifuged sperm samples was assessed as follows: subjective motility assessment, sperm morphology (8, 9) and chromatin integrity using the method of Evenson et al (10) modified by Januskauskas et al, (11, 12).

For subjective motility assessment, aliquots (0.5 4) of the extended ejaculate and sperm preparations were examined by phase contrast light microscopy (×200) immediately after preparation, on a heated microscope stage (38° C.), and once daily until the motility had dropped to approximately 20%. Sperm preparations were stored either in the refrigerator (6° C.) or at room temperature (22-30° C.). When assessing the motility of spermatozoa which had been stored at 6° C., the samples were allowed to stand at room temperature for 15 minutes before aliquots were taken for motility assessment.

In the second experiment, extended ejaculates (n=21) were stored overnight in an insulated transport box containing cold packs, i.e. using the standard method for transporting stallion semen. Either density gradient or single layer centrifugations were carried out on the following day using the stored extended semen, with motility estimates being made on the sperm preparations from both fresh and stored ejaculates.

Results: When fresh, extended semen was used for colloid centrifugation, the proportion of motile spermatozoa, morphologically normal spermatozoa and spermatozoa with intact chromatin were similar for the two centrifugation methods. These parameters of sperm quality following either method of colloid centrifugation were better than in the uncentrifuged samples (Table 1) and length of sperm survival was significantly improved, ranging from 4 days to 10 days at 6° C. and from 2 to 6 days at room temperature.

TABLE 1

Effect of single layer centrifugation and density gradient centrifugation on stallion sperm quality, mean ± SD (n = 38).

| Parameter | Uncentrifuged control | After colloid centrifugation | |
|---|---|---|---|
| | | Single layer | Density gradient |
| Motility (%) | 68.0 ± 9.2 | 84.7 ± 5.4 ᵃ ᵇ | 84.3 ± 5.9 ᵃ ᵇ |
| Yield | | 27.0 ± 6.6 ᵇ | 32.6 ± 7.8 ᵇ |
| Survival at 4° C. (days) | 2.4 ± 1.3 | 5.6 ± 1.8 ᵃ ᵇ | 5.7 ± 1.9 ᵃ ᵇ |
| | Range 1-5 | Range 3-9 | Range 3-10 |
| Survival at room temperature (days) | 2.1 ± 0.7 | 3.0 ± 0.9 ᵃ ᵇ | 3.1 ± 0.9 ᵃ ᵇ |
| | Range 1-3 | Range 2-6 | Range 2-5 |
| Normal morphology (%) | 67.5 ± 13.0 | 77.1 ± 9.3 ᵃ ᵇ | 76.7 ± 8.7 ᵃ ᵇ |

TABLE 1-continued

Effect of single layer centrifugation and density gradient centrifugation on stallion sperm quality, mean ± SD (n = 38).

| Parameter | Uncentrifuged control | After colloid centrifugation | |
|---|---|---|---|
| | | Single layer | Density gradient |
| Chromatin damage (%) | 11.0 ± 4.6 | 4.8 ± 2.6 ᵃ ᵇ | 4.8 ± 2.8 ᵃ ᵇ |

ᵃ significant difference after centrifugation;
ᵇ no difference between methods.

When cold-stored semen was used for centrifugation, the yield was reduced by 18-20% compared to fresh semen, and more variation between ejaculates was observed than for fresh ejaculates. Again, sperm motility and sperm survival were improved in the centrifuged sperm preparations compared to stored, unprocessed ejaculates (FIG. 1).

Conclusions: the two colloid centrifugation techniques produce equivalent sperm preparations, with improved sperm quality compared to uncentrifuged control samples. SLC or DGC could be carried out with stored semen as well as with fresh semen, although sperm quality in the resulting sperm preparations was better when fresh semen was used. Since SLC is simpler and quicker to carry out than DGC, it would be convenient for use in the field.

Example 2

Stallion

Objectives: (i) to investigate the changes in sperm motility, viability and chromatin integrity with storage after colloid centrifugation; (ii) to investigate the necessity of washing the sperm pellet by retrospective data analysis.

Methods: semen was collected from 4 stallions at commercial AI studs using standard methods. The ejaculates were extended using home-made or commercially available semen extenders (Kenneys' extender, INRA 96) warmed to 37° C. and the sperm concentration was adjusted to ca. 100×10⁶/ml. Aliquots from these ejaculates were used for SLC as described previously, using 1.5 mL extended ejaculate layered on top of 4 mL colloid (80%). The sperm pellet was not washed. Sperm quality (sperm motility, sperm viability, membrane integrity and chromatin integrity) was assessed in SLC-prepared and uncentrifuged control samples immediately and after 24 and 48 h. Methods are as described in Example 1, with the addition of the method for computerized analysis of sperm motility (CASA) (13) sperm viability and membrane integrity (14). Sperm preparations were stored in the refrigerator (6° C.). When assessing the motility of spermatozoa which had been stored at 6° C., the samples were allowed to equilibrate at room temperature for 15 minutes before making the assessment.

For the retrospective analysis, a comparison was made of the subjective motility data from 38 ejaculates prepared by single layer centrifugation with subsequent washing of the sperm pellet and 39 ejaculates where there was no washing of the sperm pellet after single layer centrifugation.

Results: there was a rapid deterioration in sperm motility in the uncentrifuged samples over 48 h, accompanied by a decrease in sperm viability, membrane integrity and chromatin integrity. In contrast, in the SLC-prepared samples, all these parameters of sperm quality were better than in the uncentrifuged samples and were retained over 48 h (Tables 2-5).

TABLE 2

Motility parameters (subjective and CASA) for sperm samples before colloidal centrifugation, immediately after colloidal centrifugation and at 24 h and 48 h after colloidal centrifugation while stored at 5° C. (10 ejaculates).

| Sample | Time | Subjective motility | CASA total motility | C-mot | Non l-mot | l-mot |
|---|---|---|---|---|---|---|
| Un-centrifuged | 0 | 64 ± 3.9 | 72.11 ± 13.1 | 2.26 ± 0.93 | 46.7 ± 14.4 | 34.8 ± 22.9 |
|  | +24 | 31.5 ± 15.1 | 33.3 ± 19.4 | 4.77 ± 5.4 | 59.95 ± 9.4 | 9.69 ± 8.6 |
|  | +48 | 10 ± 6.6 | 12.1 ± 12.2 | 1.97 ± 2.4 | 45.9 ± 21.3 | 10.3 12.4 |
| Centrifuged | 0 | 77 ± 7.5 | 85.7 ± 9.0 | 5.6 ± 3.6 | 27.1 ± 14.3 | 59 ± 18.1 |
|  | +24 | 72.5 ± 18.7 | 71.3 ± 2.34 | 12.25 ± 6.2 | 31.0 ± 22.0 | 49.8 ± 23.1 |
|  | +48 | 48.5 ± 14.9 | 61.7 ± 2.7 | 10.97 ± 4.9 | 38.31 ± 25.0 | 44.68 ± 23.2 |

Note:
CASA motility = total motile population according to CASA;
C-mot = circular motility;
non-l mot = non-linear motility;
l-mot = linear progressive motility.
1) Subjective motility: centrifuged samples had significantly greater motility than non-centrifuged samples at all time points (P < 0.001).
2) CASA: Centrifuged samples had greater motility than uncentrifuged samples at all time points (0 h, P < 0.05, 24 and 48 h P < 0.001); values for c-mot and l-mot were significantly higher for centrifuged samples than uncentrifuged samples at all time points whereas values for non l-mot were significantly lower (P < 0.05).

TABLE 3

Effect of storage at 5° C. on sperm viability (SYBR-14/PI staining) in unselected and SLC-selected sperm samples over time (n = 10).

| | Unselected | | | SLC-selected | | |
|---|---|---|---|---|---|---|
| | living | dead | dying | living | dead | dying |
| 0 | 64.7 ± 9.3$^{b\,d}$ | 27.4 ± 9.1$^{ad}$ | 7.9 ± 2.6$^{b}$ | 79.5 ± 9.2$^{b}$ | 16.4 ± 8.1$^{a}$ | 4.1 ± 2.0$^{b}$ |
| +24 | 50.3 ± 18.3$^{cd}$ | 40.0 ± 20.7$^{b}$ | 10.0 ± 4.7$^{b}$ | 79.1 ± 8.8$^{c}$ | 15.9 ± 6.7$^{b}$ | 5.0 ± 2.6$^{b}$ |
| +48 | 32.8 ± 10.9$^{c\,d}$ | 56.8 ± 24.8$^{cd}$ | 10.5 ± 6.8 ns | 75.6 ± 6.8$^{c}$ | 18.5 ± 5.6$^{c}$ | 5.9 ± 2.0 ns |

$^{a,\,b,\,c}$ = significant difference between uncentrifuged and centrifuged samples P < 0.05, P < 0.01, P < 0.001 respectively.
$^{d}$ = significant difference between uncentrifuged samples at different time points P ≤ 0.05

TABLE 4

Changes in plasma membrane stability of stallion spermatozoa with storage at 5° C.; Annexin V/propidium iodide staining (n = 10).

| | AN−/PI− | | AN−/PI+ | | AN+/PI+ | | AN+/PI− | |
|---|---|---|---|---|---|---|---|---|
| Time | un-selected | SLC | un-selected | SLC | un-selected | SLC | un-selected | SLC |
| 0 | 69.3 ± 8.2ns$^{b}$ | 74.6 ± 7.6ns | 23.9 ± 6.0$^{a\,b}$ | 13.4 ± 3.3$^{a}$ | 4.8 ± 3.3$^{a}$ | 9.1 ± 4.4$^{a}$ | 2.0 ± 0.4$^{a\,b}$ | 2.9 ± 0.5$^{a}$ |
| 24 | 67.1 ± 12.2ns | 74.1 ± 10.4ns | 28.7 ± 11.9$^{a}$ | 13.1 ± 2.8$^{a}$ | 2.5 ± 1.3$^{a}$ | 7.9 ± 5.6$^{a}$ | 1.7 ± 0.9$^{a}$ | 5.0 ± 3.7$^{a}$ |
| 48 | 56.6 ± 14.7$^{a\,b}$ | 74.9 ± 5.5$^{a}$ | 39.1 ± 14.7$^{a\,b}$ | 15.7 ± 4.1$^{a}$ | 3.1 ± 1.1$^{a}$ | 7.0 ± 2.9$^{a}$ | 1.3 ± 0.8ns$^{b}$ | 2.4 ± 1.5ns |

Note:
AN−/PI− = living spermatozoa with stable membranes;
AN+/PI− = spermatozoa with unstable but intact membranes;
AN−/PI+ and AN+/PI+ = spermatozoa with damaged membranes.
SLC = single layer centrifugation
$^{a}$ = significant difference between uncentrifuged and centrifuged samples, P ≤ 0.05.
$^{b}$ = significant difference between uncentrifuged samples at 0 h and 48 h, P ≤ 0.05.
ns = not significant

TABLE 5

Effect of storage on chromatin integrity in unselected and selected sperm samples over time using the Sperm Chromatin Structure Assay (SCSA) (n = 10).

| | Unselected | | | Selected | | |
|---|---|---|---|---|---|---|
| | DFI | Mean_DFI | SD-DFI | DFI | Mean_DFI | SD-DFI |
| 0 | 22.1 ± 9.7[a] | 414.9 ± 34.0[b] | 23.8 ± 3.99 | 11.3 ± 4.9[a] | 414.9 ± 31.7[b] | 24.2 ± 3.9 |
| +24 | 29.6 ± 10.0[a] | 413.8 ± 42[b] | 21.8 ± 3.1[b] | 14.8 ± 6.8[a] | 412.2 ± 35.2[b] | 30.5 ± 2.3[b] |
| +48 | 41.1 ± 20.3[b] | 393.8 ± 45.6 | 21.3 ± 3.3[a] | 11.6 ± 5.3[b] | 418.6 ± 37.0 | 28.3 ± 3.7[a] |

[a] = significant difference between uncentrifuged and centrifuged samples, P < 0.01
[b] = significant difference between uncentrifuged and centrifuged samples, P < 0.001.

In The retrospective comparison of washing and not washing the sperm pellet after single layer centrifugation, there was no difference in the mean subjective motility of the SLC-prepared sperm preparations (FIG. 2).

Conclusions: sperm quality (motility, viability and chromatin integrity) in centrifuged samples is retained during storage for 48 h, either at 6° C. or at room temperature, whereas the sperm quality of uncentrifuged samples deteriorated. Washing of the sperm pellet after single layer centrifugation is not an absolute requirement in terms of sperm quality and therefore this stage can be omitted to save time.

Example 3

Stallion

Objective: to investigate the effect of osmolarity and density of the colloid formulations on yield and quality of stallion sperm samples, and also the use of centrifuge tubes of different materials (glass versus plastic) and different sizes (10 vs. 50 mL) on sperm recovery rate from colloid centrifugation (SLC).

Methods: colloid centrifugation was performed as described previously with the following modifications according to the different investigations: (i) Colloids of two osmolarities, 320 and 345 mOsm, were used for single layer centrifugation and density gradient centrifugation of aliquots of 15 stallion ejaculates; (ii) colloids (4 mL) of different densities were used for SLC as follows: 40% (low density), 60% (intermediate density) and 80% (standard density); (iii) aliquots of 7 ejaculates were prepared by SLC in glass and plastic centrifuge tubes; (iv) a comparison was made using SLC or DGC in small tubes (gradient 2+2+2.5 mL, single layer 4+1.5 mL) and large tubes (gradients 4+4+3, 5+5+4.5, 9+9+6 and 9+9+7.5; single layer 8+3, 8+4.5 and 12+3) on one occasion each. Numbers refer to the volume in the bottom layer, volume in the upper layer (for density gradients), or for volume in single layer, and volume of extended ejaculate respectively. Parameters used to evaluate sperm quality in all these studies were subjective sperm motility and recovery rate (yield), and also sperm morphology and chromatin integrity for the comparison of different osmolarities, as described previously.

Results (i): the recovery rate was slightly lower for higher osmolarities of colloid compared to the normal osmolarity, although these differences were not statistically significant (Table 1). Sperm survival was not affected by colloid osmolarity.

TABLE 6

Effect of osmolarity of colloid on number of motile spermatozoa in the pellet after centrifugation on a colloid (mean ± SD). n = 20

| 305-320 mOsm | | 330-345 mOsm | |
|---|---|---|---|
| Single layer | Density gradient | Single Layer | Density gradient |
| 30.19 × 10⁶ ±16.9 | 31.84 × 10⁶ ±19.7 | 25.8 × 10⁶ ±18.5 | 26.46 × 10⁶ ±20.0 |

Use of a high osmolarity colloid resulted in an increase in the number of morphologically normal spermatozoa in the preparation (P<0.001) (FIG. 3). Furthermore, this trend was also observed for density gradients, although here the difference was not quite statistically significant (P<0.051).

For individual morphological abnormalities, however, differences in the ability of the normal and high osmolarity colloid formulations to remove abnormal spermatozoa were not significant. In contrast, use of a high osmolarity colloid for the single layer did not increase the effectiveness of removal of spermatozoa with damaged chromatin (FIG. 4).

Results (ii:) After centrifugation through a single layer of low density, the sperm preparations were very similar to the control (uncentrifuged semen) in terms of numbers of motile spermatozoa, presence of cellular debris etc. However, sperm survival was extended by approximately 24 hours in the centrifuged preparations (FIG. 5). When the spermatozoa were prepared on a single layer of an intermediate density, the preparations contained a higher proportion of motile spermatozoa, and these spermatozoa survived longer than controls (uncentrifuged aliquot), although neither parameter was as good as in the samples prepared on the normal single layer (FIG. 6). Sperm numbers were increased substantially (P<0.01) for the samples prepared on the 60% colloid compared to the usual 80% colloid (mean±SD: 72.6±28.9 million compared to 28.9±24.7 million).

Results (iii): Use of glass instead of plastic centrifuge tubes for seven ejaculates resulted in a significant increase (P<0.01) in the number of spermatozoa appearing in the pellets. Mean values were 42.2 million and 39.3 million for glass and plastic tubes respectively.

Results (iv): there were considerable differences in yield between ejaculates for one stallion, expressed as a proportion of the initial load. The scale-up gradients consistently gave smaller yields than the usual gradient, but two of the larger volumes of colloid used as a single layer, and one of the gradients, produced larger yields than the usual size of single layer (FIG. 7). Increasing the volumes above these levels did not increase recovery. The proportion of motile spermatozoa was reduced slightly in the large tube compared to the small tube (mean 75% cf. 80%), irrespective of which volume combination was used. Length of sperm survival was not affected by the scale-up.

Conclusions: the yield of stallion spermatozoa obtained after SLC can be increased by lowering the density of the colloid used for a single layer, although sperm quality is not as good as when the normal density is used. Yield may also be increased by scaling-up into larger centrifuge tubes. Using glass centrifuge tubes instead of plastic increases the yield slightly but may not be worth the additional expenses involved in purchasing, cleaning and sterilizing the tubes. Increasing the osmolarity of the colloid formulation from 320 mOsm to 345 mOsm results in improved normal sperm morphology, but not chromatin integrity, although sperm yield may be decreased.

Example 4

Stallion

Objective: to scale-up the colloid centrifugation technique to facilitate processing of whole ejaculates in the field.

Experiments: (i) use of the 80% colloid in 50 mL tubes and in 200 mL tubes (experiment 1); (ii) investigating the effect of changing the density of the colloid (60% to 80%) in 50 mL tubes (experiment 2); (iii) using the 80% colloid in 10 mL tubes but increasing the volume of extended ejaculate used (experiment 3); and (iv) comparing 80% colloid in 10 mL tubes with 1.5 mL and 4.5 mL ejaculate on top and 67.5% colloid in 50 mL tubes with 15-18 mL ejaculate on top.

Experiment 1: Aliquots from 8 ejaculates (4 stallions, Västerbo Stuteri) were transported to the laboratory and used for SLC as described above, designated small (1.5 mL extended ejaculate on 4 mL colloid in a 10 mL tube) and large (7.5 mL extended ejaculate on 20 mL colloid in a 50 mL Falcon tube). These volumes of colloid represent columns of the same height in the two types of centrifuge tube. After centrifugation at 300 g for 20 min, the resulting sperm pellets were resuspended in fresh Kenney's extender in a clean tube, using 1 mL Kenney's extender for the "small" pellet and 5 mL Kenney's extender for the "large" pellet. Sperm quality was assessed in the SLC-selected sperm preparations and the unselected sperm preparations for subjective motility, CASA, sperm viability (SYBR-14/PI staining), membrane integrity (Annexin-V/PI staining) and sperm chromatin integrity using SCSA, as described previously. The number of spermatozoa in each sperm pellet was used to calculate the yield. The analyses were repeated after 24 storage at 5° C. for 24 and 48 h. Subjective motility assessments were continued until sperm motility was <20%. Aliquots from a further 4 ejaculates were used for SLC as described above designated small (1.5 mL extended ejaculate on 4 mL colloid in a 10 mL tube), while 22.5 mL of the same ejaculate were layered on top of 60 mL colloid in 200 mL Falcon tubes, designated extra large (SLC-XL). The SLC-XL sperm pellets were resuspended in 10 mL Kenney's extender. Both small and large sperm preparations were assessed for sperm motility and duration of survival. The methods were as described previously.

Results:

Sperm motility: Total motility was improved in the SLC-selected sperm preparations compared to the unselected ones, both according to subjective motility estimations and by CASA. According to subjective motility assessments, these differences were significant at all time points (P<0.001) and there were no differences between SLC-small and SLC-large (FIG. 8). A similar result was obtained for the SLC-XL and SLC-small samples (FIG. 9).

The CASA results also showed the differences between unselected and SLC-selected sperm samples to be significant at all time points (P<0.05), although there were also some differences between the SLC-small and SLC-large (P<0.05), with the small preparations having better motility than the large (Table 7). For circular motility, non-linear motility and linear motility, there were significant differences between SLC-selected and unselected sperm preparations (P<0.05), but not between SLC-small and SLC-large preparations. There was a good correlation between subjective and CASA assessments for total motility (r=0.8, P<0.001).

TABLE 7

Motility assessments (Subjective and Computer Assisted Motility Analysis) of small and large Single Layer Centrifugation sperm preparations (Means ± sd) for total motility and various motility parameters.

| Sample | Time (h) | Subjective motility (%) | CASA motility (%) | Circular motility (%) | Non linear motility (%) | Linear motility (%) |
|---|---|---|---|---|---|---|
| Unselected | 0 | 64 ± 3.9 | 72.11 ± 13.1$^a$ | 2.26 ± 0.93$^{ab}$ | 46.7 ± 14.4 | 34.8 ± 22.9 |
|  | +24 | 31.5 ± 15.1$^a$ | 33.3 ± 19.4$^{ac}$ | 4.77 ± 5.4$^{ac}$ | 59.95 ± 9.4 | 9.69 ± 8.6 |
|  | +48 | 10 ± 6.6 | 12.1 ± 12.2$^c$ | 1.97 ± 2.4 | 45.9 ± 21.3 | 10.3 12.4 |
| Selected small | 0 | 77 ± 7.5 | 85.7 ± 9.0$^a$ | 5.6 ± 3.6$^b$ | 27.1 ± 14.3 | 59 ± 18.1 |
|  | +24 | 72.5 ± 18.7$^{af}$ | 71.3 ± 2.34$^c$ | 12.25 ± 6.2$^c$ | 31.0 ± 22.0 | 49.8 ± 23.1 |
|  | +48 | 48.5 ± 14.9 | 61.7 ± 2.7$^c$ | 10.97 ± 4.9 | 38.31 ± 25.0 | 44.68 ± 23.2 |
| Selected large | 0 | 77 ± 8.6 | 80.22 ± 10.0$^a$ | 6.9 ± 3.9$^a$ | 29.0 ± 16.8 | 57.8 ± 18.7 |
|  | +24 | 69 ± 15.4$^f$ | 56.8 ± 20.7$^a$ | 13.1 ± 7.5 | 33.6 ± 19.8 | 46.8 ± 24.2 |
|  | +48 | 54.5 ± 9.8 | 42.3 ± 18.3$^c$ | 10.5 ± 5.6 | 39.6 ± 31.0 | 44.2 ± 27.6 |

$^a$= difference between unselected and SLC-selected, P < 0.05.
$^f$= difference between small and large SLC-selected, P < 0.05.

Sperm viability: FIG. 10 shows the results of the SYBR-14/PI staining in small and large SLC-selected and unselected sperm preparations. The proportion of living spermatozoa was significantly higher in the SLC-selected sperm preparations than in the unselected sperm preparations, whereas the proportions of dead or dying spermatozoa were significantly less in the selected than in the unselected sperm preparations. There were no differences in these proportions between SLC-large and SLC-small sperm preparations. With time, the proportion of living spermatozoa decreased significantly in the unselected sperm preparations while the proportion of dead spermatozoa rose significantly (P<0.05). In contrast, these proportions did not change in the SLC-selected sperm preparations. For the SLC-XL preparations, there was no difference between mean values for SLC-small and SLC-XL sperm preparations for any parameter (Table 8).

TABLE 8

Sperm viability in unselected, Small and Extra Large Single Layer
Centrifugation sperm preparations using SYBR-14/PI staining (Means ± sd)
(n = 4).

|  | Small | | | Extra Large | | |
|---|---|---|---|---|---|---|
|  | Living | Dead | Dying | Living | Dead | Dying |
| 0 h | 82.8 ± 4.9 | 14.7 ± 5.3 | 2.5 ± 0.3 | 85.4 ± 2.5 | 12.2 ± 1.8 | 2.3 ± 0.8 |
| 24 h | 83 ± 6.2 | 14.2 ± 6.3 | 2.7 ± 0.3 | 86.1 ± 1.9 | 11.1 ± 1.7 | 2.9 ± 0.9 |
| 48 h | 78.8 ± 7.9 | 17.7 ± 8.7 | 3.5 ± 1.1 | 80.3 ± 4.3 | 15.0 ± 4.1 | 4.6 ± 2.2 |

Note:
No significant difference between SLC-small and SLC-XL single layer preparations.
Values for each parameter did not change significantly with time for either SLC-small or SLC-XL.

Sperm membrane integrity: the results of the Annexin-V/PI staining are shown in Table 9 (SLC-small versus SLC-large) and Table 10 (SLC-small versus SLC-XL). There was no difference between the SLC-small and SLC-large sperm preparations at any time points: the only differences between unselected and selected sperm preparations stain with Annexin-/PI-(intact membranes) was for SLC-small sperm preparations at time 0 h ($P<0.05$). There were also significant differences between unselected and SLC-selected sperm preparations in several of the other parameters: between unselected and SLC-selected preparations at 0 h, 24 h and 48 h for Annexin-/PI+($P<0.001$); between unselected and SLC-selected preparations at 24 and 48 h for Annexin+/PI+ ($P<0.001$); between unselected and SLC-small preparations at 0 h and 48 h, and between unselected and SLC-large preparations at 24 h for spermatozoa stained with Annexin+/PI- ($P<0.001$). There were no significant differences between SLC-small and SLC-XL for any of the parameters measured, nor did the values change significantly with time.

TABLE 9

Sperm membrane integrity in unselected and small- and large-single
layer centrifugation sperm preparations using Annexin–V/Propidium iodide
staining (means ± sd) (n = 8).

| Time | Treatment | Annexin–V–/PI– | Annexin–V–/PI+ | Annexin–V+/PI+ | Annexin–V+/PI– |
|---|---|---|---|---|---|
| 0 h | large | 74.2 ± 8.7 | 13.8 ± 6.1$^c$ | 8.4 ± 3.2 | 3.6 ± 2.0 |
|  | small | 75.2 ± 6.0$^a$ | 12.8 ± 2.8$^c$ | 8.8 ± 3.4$^c$ | 3.2 ± 0.6 |
|  | unselected | 67.4 ± 8.1$^a$ | 24.7 ± 6.0$^{cd}$ | 5.7 ± 3.5$^c$ | 2.3 ± 0.6 |
| 24 h | large | 69.1 ± 14.8 | 13.8 ± 3.4$^c$ | 11.6 ± 8.9$^a$ | 5.5 ± 4.1$^b$ |
|  | small | 75.0 ± 9.3 | 12.7 ± 3.3$^c$ | 7.1 ± 3.6 | 5.3 ± 4.1$^{ce}$ |
|  | unselected | 65.1 ± 13.1 | 30.3 ± 12.5$^c$ | 2.5 ± 1.3$^a$ | 2.1 ± 1.1$^{b\,c}$ |
| 48 h | large | 73.3 ± 6.4 | 15.1 ± 3.9$^c$ | 8.3 ± 2.7$^a$ | 3.4 ± 1.9$^c$ |
|  | small | 76.9 ± 4.2 | 15.2 ± 4.4$^c$ | 6.1 ± 1.6 | 2.1 ± 1.6$^{ce}$ |
|  | unselected | 51.3 ± 16.3 | 43.6 ± 16.1$^{cd}$ | 3.7 ± 1.5$^a$ | 1.3 ± 0.9$^c$ |

Note:
no differences between large and small SLC-selected sperm preparations at any time points.
$a, b, c$ = difference between unselected and selected, $P < 0.05$, $P < 0.01$, $P < 0.001$;
$d$ = difference between 0 and 24 h, $P < 0.05$;
$e$ = difference between 24 and 48 h, $P < 0.05$

TABLE 10

Sperm membrane integrity in unselected and Small and Extra Large
single layer centrifugation sperm preparations using Annexin–V/Propidium
iodide staining (means ± sd) (n = 4).

|  | SLC-Small | | | | SLC-Extra Large | | | |
|---|---|---|---|---|---|---|---|---|
|  | Annexin–V–/PI– | Annexin–V–/PI+ | Annexin–V+/PI+ | Annexin–V+/PI– | Annexin–V–/PI– | Annexin–V–/PI+ | Annexin–V+/PI+ | Annexin–V+/PI– |
| 0 h | 76.8 ± 4.8 | 11.4 ± 1.6 | 8.9 ± 3.9 | 2.8 ± 0.3 | 76.9 ± 7.8 | 13.8 ± 3.8 | 5.7 ± 1.9 | 3.7 ± 2.2 |
| 24 h | 81.9 ± 3.8 | 9.5 ± 2.4 | 5.4 ± 3.1 | 3.2 ± 1.7 | 78.7 ± 3.9 | 13.1 ± 4.1 | 4.4 ± 1.8 | 3.8 ± 2.5 |
| 48 h | 80.0 ± 2.3 | 12.9 ± 4.3 | 5.5 ± 1.3 | 1.71 ± 1.5 | 80.8 ± 4.8 | 14.0 ± 6.8 | 3.4 ± 1.7 | 1.7 ± 0.7 |

Note:
No significant difference between SLC-small and SLC-XL single layer preparations.
Values for each parameter did not change with time for either small or XL.

Sperm chromatin integrity (SCSA): the SLC-selected sperm preparations had better sperm chromatin integrity, as shown by a lower value for DFI, than the unselected sperm preparations (Table 11), at all time points (0 h, P<0.01; 24 and 48 h, P<0.001). There were no differences in either mean_DFI or SD_DFI between the unselected and selected sperm samples. For the XL samples, there was no difference between small and large for either DFI or SD_DFI (DFI small 11.2±3.8 9, XL.3±4.6; SD_DFI small 29.6±3.2, XL 27.4±6.0). However, there was a significant difference between small and XL mean_DFI (416.3±42.8 and 258.3±6.5 respectively; P<0.05).

TABLE 11

Parameters of the Sperm Chromatin Structure Assay for unselected, small SLC-selected and Large SLC-selected sperm preparations stored for 48 h at 5° C. (n = 8).

| | Unselected | | | Small SLC selected | | | Large SLC-selected | | |
|---|---|---|---|---|---|---|---|---|---|
| | DFI | Mean_DFI | SD-DFI | DFI | Mean_DFI | SD-DFI | DFI | Mean_DFI | SD-DFI |
| 0 h | 26.2 ± 6.5$^a$ | 405.4 ± 73.4 | 24.2 ± 4.1 | 14.3 ± 5.4$^a$ | 397.2 ± 71.1 | 24.3 ± 5.1 | 13.1 ± 6.4$^a$ | 400.2 ± 71.5 | 27.0 ± 4 |
| 24 h | 33.0 ± 6.6$^b$ | 415.1 ± 61.8 | 22.4 ± 3.8 | 16.0 ± 7.5$^b$ | 398.8 ± 67.4 | 28.9 ± 5.9 | 16.0 ± 7.1$^b$ | 393.4 ± 71.6 | 29.0 ± 4.1 |
| 48 h | 48.6 ± 20.1$^b$ | 404.3 ± 44.8 | 21.4 ± 3.3 | 13.8 ± 5.9$^b$ | 404.8 ± 69 | 26.0 ± 6.4 | 14.3 ± 6.6$^b$ | 394.1 ± 71.1 | 27.4 ± 4.0 |

Note:
$^{a, b}$= DFI for unselected > SLC-selected, P < 0.01 and P < 0.001 respectively.

Sperm Yield: there was a considerable difference between the mean yield for SLC-small and SLC-large sperm preparations (32±22.3% vs 8.9±8.9% respectively, P<0.001). In contrast, in a different experiment, the yields for the XL samples were approximately 25% higher than for the small samples (25.5±14.1% compared to 20.2±5.9%).

Experiment 2: Aliquots from 23 ejaculates (from 4 stallions at Västerbo Stud and 10 stallions at Flyinge AB) were used for SLC as described above, designated small (1.5 mL extended ejaculate on 4 mL colloid in a 10 mL tube) and large (7.5 mL extended ejaculate on either 15 mL or 20 mL colloid of different densities—60%, 65%, 70%, 75% or 80%—in a 50 mL Falcon tube). Note: it was not possible to use aliquots from each ejaculate for each of the 10 treatments in Experiment 2 because of shortage of sample.

After centrifugation at 300 g for 20 min, the resulting sperm pellets were retrieved and resuspended in fresh Kenney's extender in a clean tube, using 1 mL Kenney's extender for the "small" pellet and 5 mL Kenney's extender for the "large" pellet. Sperm quality in the resulting sperm preparations was assessed for subjective sperm motility and chromatin integrity as described in Experiment 1, and also sperm survival and yield. In addition, objective motility assessment was performed using either the Qualisperm™ (15) system (Flyinge ejaculates; 9) or the MTM Motion Analyzer (13) (Vasterbo ejaculates).

Results: Mean subjective motility assessment and Qualisperm™ motility measurements for the different volume/density combinations are shown in Table 12, together with survival i.e. duration of motility. Although there were no differences between the various volume/density combinations by subjective motility assessment, there were significant differences between the small and large sperm preparations at lower colloid densities using objective motility assessment with Qualisperm™. The large sperm preparations did not retain motility for as long as the small preparations (P<0.001).

TABLE 12

Effect of altering the volume and/or density of colloid used for scale-up preparations of stallion spermatozoa on mean sperm motility and survival (n = 23).

| Volume/density | Treatment | Subjective Motility (%) | Objective Motility (%)* | Survival (hours) |
|---|---|---|---|---|
| 15/60 | Small | 85 ± 0 | 76.5 ± 20.6 | 112 ± 27.7 |
| | Large | 83 ± 7.6 | 72.1 ± 16.4 | 160 ± 13.9 |
| 15/65 | Small | 86.7 ± 2.9 | 87.1 ± 3.6* | 136 ± 36.7 |
| | Large | 81.7 ± 14.4 | 59.9 ± 5.9* | 144 ± 41.6 |

TABLE 12-continued

Effect of altering the volume and/or density of colloid used for scale-up preparations of stallion spermatozoa on mean sperm motility and survival (n = 23).

| Volume/density | Treatment | Subjective Motility (%) | Objective Motility (%)* | Survival (hours) |
|---|---|---|---|---|
| 15/70 | Small | 91.7 ± 2.9* | 86.9 ± 2.6 | 120 ± 24.0 |
| | Large | 80 ± 5.0* | 82 ± 7.9 | 144 ± 24.0 |
| 15/75 | Small | 81.5 ± 5.8 | 86.4 ± 14.4 | 112 ± 27.7 |
| | Large | 80 ± 10 | 91.6 ± 3.8 | 112 ± 13.9 |
| 15/80 | Small | 85 ± 5 | 69.7 ± 16.1 | 112 ± 36.7 |
| | Large | 81.7 ± 14.4 | 73.3 ± 14.5 | 112 ± 27.7 |
| 20/60 | Small | 90 ± 0* | ND | 96 ± 24 |
| | Large | 80 ± 5* | ND | 80 ± 36.7 |
| 20/65 | Small | 90 ± 0 | ND | 112 ± 13.9 |
| | Large | 85 ± 5 | ND | 72 ± 41.6 |
| 20/70 | Small | 86.7 ± 5.8 | ND | 192 ± 98.0 |
| | Large | 80 ± 0 | ND | 104 ± 50.0 |
| 20/80 | Small | 76.7 ± 8.2 | ND | 84 ± 29.4 |
| | Large | 77.5 ± 6.89 | ND | 92 ± 18.1 |

Notes:
*Qualisperm ™. 1) Motility: No significant differences among large preparations. Significant differences among treatments for Small sized preparations: 15/70 vs. 15/60 P < 0.05; 15/70 vs. 15/80 P < 0.05; 15/70 vs. 20/80 P < 0.05; 20/60 vs. 20/80 P < 0.05; 20/65 vs. 20/80 P < 0.05. 2) Survival: No significant differences among Small size preparations; large preparation 20/65 had significantly shorter survival than large preparation 15/60; no significant differences among other large preparations.
Note:
small, 0 h vs 24 h NS. Large 0 h vs 24 h, NS. Small vs. large, 0 h P < 0.05; 24 h NS.

The DFI results (Table 13) again indicated that there were differences between the control (SLC-small) preparations and the SLC-large preparations where lower densities of colloid were used e.g. 60% and 65% (P<0.05 at 0 h) but not where 70% or greater was used. However, these differences disappeared at 24 h. There was no significant difference between DFI for SLC-small preparations at 0 h and 24 h, or for SLC-large preparations at 0 h and 24 h.

TABLE 13

Effect of altering the volume and/or density of colloid used for scale-up preparations of stallion spermatozoa on mean values of DFI (%) (n = 23).

| Volume/density | Treatment | DFI (%) 0 h | DFI (%) 24 h |
|---|---|---|---|
| 15/60 | Small | 8.6 ± 4.4 | 11.3 ± 6.7 |
| | Large | 13.7 ± 7.5 | 10.2 ± 4.3 |
| 15/65 | Small | 14.92 ± 1 | 5.2 ± 1 |
| | Large | 11.63 ± 1 | 22.4± |
| 15/70 | Small | 12.2 ± 5.9 | 8.8 ± 2.6 |
| | Large | 15.2 ± 11.5 | 11.5 ± 6.4 |
| 15/80 | Small | 12.0 ± 6 | 18.6 ± 9.1 |
| | Large | 5.5 ± 1.9 | 5.0 ± 2.1 |
| 20/60 | Small | 7.5 | 7.0 |
| | Large | 12.6 | 14.3 |
| 20/65 | Small | 13.7 ± 2.9 | 18.2 ± 3.0 |
| | Large | 7.1 ± 2.1 | 8.7 ± 3.6 |
| 20/70 | Small | 5.5 | 5.0 |
| | Large | 8 | 6.9 |
| 20/80 | Small | 14.3 ± 5.4 | 16.0 ± 7.5 |
| | Large | 13.1 ± 6.4 | 16.0 ± 7.1 |

Experiment 3: "Small" sperm preparations were processed as described previously for experiments 1 and 2 using 1.5 mL from each of 7 extended ejaculates. Additional SLC were made with an increased volume of ejaculate (4.5 ml) layered on top of 4 mL colloid in 10 mL centrifuge tubes, designated "SLC-Inc" (meaning increased volume). After centrifugation, each "SLC-Inc" sperm pellet was resuspended in 3 ml fresh Kenney' extender and all sperm suspensions were stored at 5° C. Sperm concentration was determined for all SLC preparations and sperm yield calculated. The motility of the sperm preparations and the extended ejaculate was assessed daily using CASA (13), while membrane integrity was measured at 24 h after SLC-preparation (14).

Results: The CASA motility results are shown in FIG. 11. There was no difference in motility between the SLC-Small and SLC-Inc sperm preparations, although there were significant differences between unselected and both types of selected sperm preparations at 24 and 48 h. The unselected sperm suspension had no measurable motility after 48 h.

Velocity data were also not different between the two types of SLC-selected sperm preparations (FIG. 12). Although the mean yield for the SLC-Inc preparations was greater than for the SLC-small (41.2±28.3% and 33.3±21.3% respectively), this difference was not statistically significant. Sperm viability was not different between the two SLC-methods (Small, living 72±0.3%; Inc, living 72±0.3%).

Experiment 4: As for experiment 3 but with the addition of a second scale-up method using 15 mL colloid (density 67.5%) plus 15 mL extended ejaculate, in a 50 mL Falcon tube (designated Large). Subjective and CASA (13) motility measurements were made daily, viability assessments were carried out at 0 h and 24 h, while aliquots were frozen for subsequent SCSA at 0 h, 24 h, 48 h and 72 h.

Results: the subjective and CASA motility results were similar to those obtained in Experiment 3 with no difference between any of the SCL-methods (FIG. 13). There was a good correlation between CASA and subjective motility results (r=0.7 to 0.9 for centrifuged and uncentrifuged samples respectively; P<0.001). The yields were not significantly different between the three SLC treatments (mean±SD: small, 33.3±20%; Inc 36.3±15.8%; large 40±21.7%). Furthermore, there was no difference in sperm viability between any of the SLC scale-up methods (Table 14).

TABLE 14

Proportion of viable spermatozoa in different SLC-sperm preparations at 0 h and 24 h, mean ± SD (n = 9).

| | Centrifugation Small volume | Centrifugation Increased volume | Centrifugation Large volume |
|---|---|---|---|
| 0 h | 78 ± 11.3 | 84.9 ± 8.9 | 81.4 ± 11.5 |
| +24 | 76.5 ± 11.3 | 81.4 ± 8.9 | 76.6 ± 9.0 |

No significant difference between any of these Centrifugation treatments

Significant differences were found in mean DFI between uncentrifuged and centrifuged samples, although there was an interaction with time, since the uncentrifuged samples showed deteriorating sperm quality with storage while the chromatin integrity of the centrifuged samples did not deteriorate with time (Table 15).

TABLE 15

Effect of different scale-up methods on chromatin integrity of stallion spermatozoa, mean ± SD (n = 9).

| | Centrifugation Small volume | Centrifugation Increased volume | Centrifugation Large volume |
|---|---|---|---|
| 0 h | 20.7 ± 10.2 | 14.2 ± 7.7 | 13.9 ± 6.8 |
| 24 | 19.2 ± 11.3 | 12.9 ± 8.0 | 19.2 ± 10.4 |
| 48 h | 15.0 ± 8.0 | 13.0 ± 8.0 | 21.0 ± 14.0 |
| 72 h | 17.0 ± 10.0 | 18.0 ± 11.0 | 22.0 ± 8.0 |

Conclusion: It is possible to scale-up the SLC by increasing the volume of extended ejaculate used on 4 mL colloid. However, for further increase in volume it is necessary to use a larger centrifuge tube and adjust the colloid density, as shown in Table 16. These adjustments produce sperm preparations which are equivalent to the original in sperm quality and yield, based on sperm motility, viability and chromatin integrity.

TABLE 16

Comparison of parameters giving comparable quality in scaled-up sperm preparations and the original preparation.

| | Colloid volume (mL) | Colloid density (%) | Volume extended ejaculate (mL) |
|---|---|---|---|
| Original | 4 | 80 | 1.5 |
| Increased volume | 4 | 80 | 4.5 |
| Large scale-up | 15 | 67.5 | 15-18 |

Example 5

Bull

Objectives: (i) to investigate the fertilising ability of bovine spermatozoa prepared either on a density gradient or on a single layer of colloid in IVF. (ii) to investigate the use of colloid centrifugation to select spermatozoa of normal size from a polymorphic population in a bull ejaculate.

Methods: For the first experiment, straws of cryopreserved bull spermatozoa were made available at the University of Gent, where the IVF trial was carried out. Prior to centrifugation, the straws of extended semen were thawed in water at 37° C. for 12 seconds and the concentration was adjusted to $100 \times 10^6$ million per mL. Colloid centrifugation was performed as described for stallion semen using 80% colloid E for the single layer centrifugation and 2 mls 40% plus 2 mLs 80% colloid E for the denisty gradient. Computerised sperm motility analysis (CASA) on the uncentrifuged controls and on both types of sperm preparation was carried out by an experienced operator using a Hamilton Thorne motility analyzer. Data were collected for the following parameters: velocity of the smoothed path, straight line velocity, curvilinear velocity, amplitude of lateral head deviation, beat cross frequency, straightness, linearity, concentration, % motility, % progressive motility, % rapid motility, % medium motility, % slow motility and % static. Standard methods (16) were used for IVM and IVF to determine the fertilisation rate (10). Culture of the fertilized oocytes was continued for 8 days, after which the % development to blastocyst and the total number of cells were assessed.

For the second experiment, ejaculates were collected from a bull known to produce both diploid and haploid spermatozoa. The spermatozoa were highly polymorphic, with macrocephalic and microcephalic spermatozoa present, together with a whole range of spermatozoa which were approximately of normal size. The semen was cryopreserved at the University of Helsinki, Finland in the usual manner. The straws were sent to SLU for further examination. Prior to centrifugation, the straws of extended semen were thawed in water at 37° C. for 12 seconds and the semen was extended with Buffer B. Single layers of colloid of different densities ranging from 40-90% of the stock colloid, were used to identify suitable densities for subsequent use in a density gradient. Colloid centrifugation was carried out as described previously, with the resulting sperm pellet being resuspended in Buffer B. Pre-stained slides (Testsimplets; Online Diagnostics, Germany) were used to stain the spermatozoa for microscopic examination. The proportion of macrocephalic spermatozoa in 200 spermatozoa from the uncentrifuged and centrifuged sperm samples was recorded.

Results (first experiment): Mean fertilisation rate, blastocyst development rate and total number of cells were 56.27%±29.1, 23.5%±17.4 and 83.2±29.9 respectively for density gradient-prepared spermatozoa, and 58.1%±23.3, 24.5%±14.3 and 94.6±23.4 respectively for spermatozoa prepared on a single layer of colloid. Mean values of various parameters of computerized analysis of sperm motility were not different between the two sperm preparation methods (Table 17).

TABLE 17

CASA parameters of bovine spermatozoa prepared by density gradient and single layer centrifugation.

| Parameter | Single Layer | Density Gradient | Parameter | Single Layer | Density Gradient |
|---|---|---|---|---|---|
| VAP | 112.36 ± 9.93 | 111.1 ± 8.87 | Conc | 37.68 ± 17.69 | 36.96 ± 20.3 |
| VSL | 95.4 ± 8.87 | 94.92 ± 10.58 | % mot | 75.4 ± 10.5 | 71.4 ± 17.09 |
| VCL | 171.48 ± 10.98 | 167.44 ± 16.18 | % prog | 61.4 ± 13.3 | 54.8 ± 16.8 |
| ALH | 7.08 ± 0.57 | 6.98 ± 0.71 | % rapid | 69.4 ± 11.04 | 64.6 ± 17.87 |
| BCF | 23.12 ± 5.63 | 23.3 ± 5.54 | % medium | 6.6 ± 1.95 | 6.6 ± 1.95 |
| STR | 82.2 ± 2.28 | 83 ± 4.04 | % slow | 14 ± 6.12 | 15.2 ± 9.49 |
| LIN | 55.6 ± 4.05 | 56.2 ± 3.70 | % static | 10.4 ± 6.69 | 13.4 ± 8.53 |

Note:
there are no significant differences.

(ii) The results of the single layer centrifugation with the polymorphic spermatozoa are shown in Table 18. Almost all of the spermatozoa were able to pass through the 40% and 50% colloid single layers. The highest proportion of macrocephalic spermatozoa was found in the pellet after a 60% single layer (49% macrocephalic), decreasing again to 27% macrocephalic when the colloid density was increased to 70%. Using a density gradient with layers 70/55%, two sub-populations were identified, one enriched for the normal sized sperm at the interface between the two layers (8% macrocephalic sperm and 92% normal), while the sperm pellet was enriched for macrocephalic sperm (34%) Using colloid densities of 55% and 70%, it was possible to obtain two sperm sub-populations, one containing nearly all normally sized spermatozoa, and the other enriched for the macrocephalic spermatozoa (Table 19). The microcephalic spermatozoa were selected out by the lowest density colloid and therefore did not appear in either of the selected sub-populations.

TABLE 18

Proportions of spermatozoa of different sizes before and after single layer centrifugation of bull spermatozoa.

| | | Large | Small | Rest |
|---|---|---|---|---|
| Before | | 24 | 6 | 70 |
| After SL 40% | Pellet | 35.5 | 1 | 63.5 |
| | Colloid (small numbers only) | 23 | 4 | 73 |
| Before | | 26 | 6 | 68 |
| After SL 60% | Pellet | 49 | 2 | 49 |
| | Colloid | 14 | 3 | 82 |
| After SL 70% | Pellet | 27 | 3.5 | 69.5 |
| | Colloid | 15 | 3.5 | 80 |

TABLE 19

Proportions of spermatozoa of different sizes before and after density gradient centrifugation of bull spermatozoa.

| | | Large | Rest | Small |
|---|---|---|---|---|
| Before | | 32 | 65 | 3 |
| After 70/55 | Pellet | 34 | 64.5 | 1.5 |
| | 70 colloid | 17 | 81.5 | 1.5 |
| | Interface | 8 | 92 | 0 |
| | Top (<55%) (small numbers) | 10 | 83.5 | 6.5 |

Conclusions:

1) spermatozoa prepared on a single layer of colloid are not different in behaviour or properties to spermatozoa prepared on a density gradient.

2) Using a combination of single layer centrifugation and density gradient centrifugation, it was possible to separate the spermatozoa into different sub-populations, e.g. one containing nearly all normally sized spermatozoa, and the other enriched for macrocephalic spermatozoa.

Example 6

Boar

Objective: (i) to investigate the effect of increasing the osmolarity of a colloid formulation and the size of centrifuge tube on the efficacy of boar sperm selection during density gradient centrifugation, with a view to developing colloid formulations specific for animal spermatozoa, (ii) to compare density gradient centrifugation with centrifugation on a single layer of colloid for preparing boar spermatozoa, (iii) the effect of autoclaving the colloid, and (iv) the effect of washing the sperm pellet after colloidal centrifugation.

Methods: the gel-free sperm-rich fraction of the ejaculate was collected from 8 boars using the gloved hand method and was immediately extended 1:1 (v/v) in Beltsville Thawing Solution. Sperm concentration was adjusted to $100 \times 10^6$/mL. Density gradient and single layer centrifugation was carried out according to the method described previously, using 80% colloid A for the single layer centrifugation and 2 mL 40% plus 2 mL 80% colloid A for the density gradient. In one experiment, replicate sperm pellets were either washed (by resuspending the pellet in 5 mL semen extender and centrifuging at 500 g for 10 min.), or not washed. Sperm motility in the unselected and selected sperm samples was assessed subjectively as follows: aliquots (0.5 µL) were examined by phase contrast light microscopy (×200), on a heated microscope stage (38° C.) immediately after preparation and subsequently on a daily basis until the motility had dropped to approximately 20%. For the assessments on subsequent days, the sperm preparations were stored overnight at room temperature (19-24° C., depending on the weather) and were incubated at 38° C. for 15-30 minutes prior to motility evaluation. Recovery rate (yield) was calculated as the proportion of spermatozoa initially loaded on top of the colloid which appeared in the sperm pellet after centrifugation.

Results: increasing the osmolarity of the colloid used for density gradient centrifugation of boar spermatozoa from 305 to 330 mOsm increased the proportion of motile spermatozoa in the resulting sperm preparation (FIGS. 14 and 15). Sperm motility was retained for at least 24 hours longer in the centrifuged sperm preparations than in controls (uncentrifuged aliquots), that is, 7 or 8 days for spermatozoa centrifuged on a density gradient compared to less than 6 days for uncentrifuged spermatozoa. For the comparison of the single layer of colloid and density gradient, sperm motility was significantly better (P<0.0.001) in the centrifuged sperm preparations (means±sd: 79.6±8.1% and 74.2±12.0% for single layer and density gradient respectively) than in the uncentrifuged controls (62.9±12.7%). The number of spermatozoa obtained after centrifugation (Table 20) and the mean yield were not different between the two methods (mean yield of motile spermatozoa, single layer: 67.5±25.6%; density gradient: 59.6%±22.3%). Sperm survival (FIG. 16) was significantly increased by colloidal centrifugation (uncentrifuged preparations 3.1±0.3 days, SL 5.5±0.79 days, DG 5.75±0.62 days; P<0.001 for uncentrifuged versus centrifuged; SL vs. DG, ns). Incubation prior to motility evaluation was necessary for stored sperm samples (FIG. 17). The presence of bacteria in the uncentrifuged sperm samples may have contributed to the demise of the spermatozoa. Colloidal centrifugation appeared to remove the bacteria (subjective visual assessment). Autoclaving the colloid formulation did not have an effect on sperm numbers, sperm motility or sperm survival (Table 21). Furthermore, washing the sperm pellet obtained after colloidal centrifugation versus not washing the sperm pellet had no effect on sperm numbers, sperm motility or sperm survival (Table 22). Boar spermatozoa could be stored for 24 hours before centrifugation without having a detrimental effect on sperm motility and duration of motility in the centrifuged preparations (FIG. 18).

TABLE 20

Number of boar spermatozoa obtained after density gradient and single layer centrifugation, mean ± standard deviation (millions) (n = 20)

| Boar | Single Layer | Density gradient | P value |
| --- | --- | --- | --- |
| 87 | 107.17 ± 20.3 | 84.5 ± 20.0 | NS |
| 1500 | 49.5 ± 28.7 | 45.2 ± 15.8 | NS |
| 62 | 88.7 ± 31.8 | 90.7 ± 25.4 | NS |
| 367 | 93.2 ± 25.5 | 90.8 ± 32.7 | NS |

Note:
Differences between boars significant (P < 0.01) but not between ejaculates.

TABLE 21

Effect of autoclaving the colloid on sperm motility, sperm survival and sperm number in the pellet.

| Parameter | Autoclaved | Not autoclaved |
| --- | --- | --- |
| Sperm motility on Day 1 (%) | 78.6 ± 8.7 | 81.4 ± 6.4 |
| Sperm survival (days) | 4.7 ± 1.2 | 4.5 ± 1.3 |
| Sperm number (×$10^6$) | 88.5 ± 30.1 | 77.5 ± 30.2 |

Note:
differences between autoclaved and non-autoclaved colloids were not significant.

TABLE 22

Effect of washing the sperm pellet after colloidal centrifugation on sperm motility, sperm survival and sperm number.

| Parameter | Washed | Not washed |
| --- | --- | --- |
| Sperm motility on Day 1 (%) | 80.7 ± 10.3 | 75.4 ± 9.9 |
| Sperm survival (days) | 6.1 ± 1.2 | 5.4 ± 1.1 |
| Sperm number (×$10^6$) | 82.5 ± 32.5 | 73.8 ± 24.1 |

Note:
differences between washed and unwashed sperm pellets were not significant.

Conclusion: increasing the osmolarity of the colloid formulation improves the selection of spermatozoa during density gradient centrifugation. Centrifugation on a single layer of colloid produces sperm preparations which are similar in motility and yield to those from density gradients, and these preparations show improved sperm motility and duration of survival compared to control (uncentrifuged) sperm samples.

Example 7

Dog

Objective: to investigate if single layer centrifugation (SLC) is beneficial in selecting good quality dog spermatozoa for insemination.

Methods: ejaculates of various sperm quality from four dogs were collected by digital manipulation. Aliquots (4.5 mL) were layered on top of 4 mL 80% colloid E in a 12-mL centrifuge tube. After centrifugation at 300 g for 20 min, the resulting sperm pellet was resuspended in egg yolk-Tris extender (1 mL) (17). An aliquot of the unselected ejaculate was extended in egg yolk-Tris extender to the same sperm concentration as the selected sperm preparation. Motility assessment using computer assisted sperm analysis (CASA) and morphological evaluation were performed on all unselected and selected sperm samples.

Results: mean sperm motility was increased from 77.2±19.6% before SLC to 87.6±2.7% after SLC while mean progressive motility was increased from 48.6±18% to 67.9±11% (Table 23). Mean normal morphology was 62.2±42.8 in unselected samples and 82.5±19.1% in SLC-selected samples. After storage for 7 days at 4° C., sperm motility was <5% in unselected sperm samples and 57±11.3% in the SLC-selected sperm preparations. The sperm yield varied from 12-47% depending on the sperm quality in the original ejaculate.

TABLE 23

Computer Assisted Sperm Analysis (CASA) motility results for unselected and SLC-selected dog sperm samples.

| Dog | Total Motility (%) | | Progressive Motility (%) | | Yield (%) |
| --- | --- | --- | --- | --- | --- |
| | unselected | selected | unselected | selected | |
| 1 | 48.3 | 84.1 | 34.3 | 81.8 | 12 |
| 2 | 82.3 | 90 | 69 | 68.5 | 47 |
| 3 | 87.9 | 89.5 | 32.5 | 54.5 | 47.5 |
| 4 | 90.4 | 86.9 | 58.7 | 67.5 | 30 |
| Mean (SD) | 77.2 (19.6) | 87.6 (2.7) | 48.6 (18) | 67.9 (11) | 34.1 (16.9) |

Conclusion: These preliminary results indicate that SLC may be a useful method for improving dog sperm quality in sperm doses for AI.

REFERENCES

1) Colenbrander, B., Gadella, B. M. and Stout, T. A. E (2003) The predictive value of semen analysis in the evaluation of stallion fertility. *Reprod. Dom Anim* 38, 305-311.
2) Malmgren, L. (1998) Effectiveness of two systems for transporting equine semen. *Theriogenology* 50, 833-839.
3) World Health Organisation. (1999) WHO laboratory manual for the analysis of human semen and sperm-cervical mucus interaction. Fourth ed. United Kingdom, Cambridge University Press.
4) Samardzija M., Karadjole, M., Matkovic, M., Cergolj, M., Getz, I., Dobranic, T., Tomaskovic, A., Petric, J., Surina J., Grizelj, J., Karadjole, T. (2006) A comparison of BoviPure and Percoll on bull sperm separation protocols for IVF. *Anim Reprod Sci* 3-4, 237-247.
5) Macpherson, M., Blanchard, T. L., Love, C. C., Brinsko, S. P., Thompson, J. A. & Varner, D. D. (2002) Use of a silane-coated silica particle solution to enhance the quality of ejaculated semen in stallions. *Theriogenology* 58, 317-320.
6) Morrell, J. M. (2006) Update on semen technologies for animal breeding. *Reprod. Dom Anim.* 40, 1-5.
7) Kenney R M, Bergman R V, Cooper W L, Morse G W. Minimal contamination techniques for breeding mares: techniques and preliminary findings. Proc. Am. Assoc. Equine Practice 1975;21,327-336.
8) Williams, W. & Utica, N. (1920) Technique of collecting semen for laboratory examination with review of several diseased bulls. *Cornell Vet* 10, 87-94.
9) Lagerlöf, N. (1934) Morphological studies on the change in sperm structure and in the testes of bulls with decreased or abolished fertility. *Acta Pathol Microbiol Scand Suppl* 19, 254-267.
10) Evenson, D P., Darzynkiewicz, Z & Melamed, M. R. (1980) Relation of mammalian sperm chromatin heterogeneity to fertility. *Science* 210, 1131-1133
11) Januskauskas, A., Johannisson, A & Rodriguez-Martinez, H. (2001) Assessment of sperm quality through fluorimetry and sperm chromatin structure assay in relation to file fertility of frozen-thawed semen from Swedish AI-bulls. *Theriogenology* 55, 947-961.
12) Januskauskas A, Johannisson A, Rodriguez-Martinez H. (2003) Subtle membrane changes in cryopreserved bull semen in relation to sperm viability, chromatin structure and field fertility. *Theriogenology* 60:743-758.
13) Kayak A, Johannisson A, Lundeheim N, Rodriguez-Martinez H, Aidnik M & S Einarsson (2003) Evaluation of cryopreserved stallion semen from Tori and Estonian breeds using CASA and flow cytometry. Anim Reprod Sci 76: 205-216.)
14) Saravia F, Hernández M, Wallgren M K, Johannisson A & H Rodríguez-Martinez (2007) Cooling during semen cryopreservation does not induce capacitation of boar spermatozoa. Int J Androl 30: 485-499.
15) Tejerina F, Buranamanuay K, Saravia F, Wallgren M & H Rodriguez-Martinez. Assessment of motility of ejaculated, liquid-stored boar spermatozoa using computerized instruments. Theriogenology 2008;69;1129-1138.
16) Tanghe, S., Van Soom, A., Sterckx, V, Maes, D & de Kruif, A. (2002) Assessment of different sperm quality parameters to predict in vitro fertility of bulls. *Reprod Domest Anim* 37, 127-132.
17) Ponglowhapen, S. Essen-Gustaysson, B. and Linde Forsberg C. (2004) Influence of glucose and fructose in the extender during long-term storage of chilled canine semen. Theriogenololgy 62, 1498-1517.

The invention claimed is:

1. A composition for separation of spermatozoa from a semen sample, the composition consisting of:
   salt selected from the group consisting of alkali metal salts and alkaline earth metal salts,
   glucose,
   EDTA,
   zwitterion buffer,
   citrate,
   silane-coated silica particles, and
   water,
said composition having a pH of 7.0-7.35 and an osmolarity of 300-345 mOsm.

2. A method for preparing spermatozoa from a semen sample from a non-human animal, comprising separating the spermatozoa from other semen constituents by centrifugation through a single layer of a colloid formulation comprising the composition according to claim 1.

3. The method according to claim 2, wherein the colloid formulation has a density in the range of 1.05-1.14 g/ml.

4. The method according to claim 2, wherein the colloid formulation has a pH of 7.0-7.3.

5. The method according to claim 2, wherein the separation is performed in a container with a volume of 10 ml or more.

6. The method according to claim 5, wherein the separation is performed in a container with a volume of 50-200 ml.

7. The method according to claim 5, wherein the colloid composition is a 65-70% buffer dilution of a stock colloid formulation having a density of about 1.13-1.14 g/ml.

8. The method according to claim 2, wherein the colloid has a height of 30-45 mm.

9. The method according to claim 2, wherein the semen sample is not oligospermic.

10. The method according to claim 2, wherein the spermatozoa are separated from seminal plasma and its cellular or non-cellular components.

11. A method for separating a sperm sub-population of interest from a semen sample from a non-human animal, comprising:
providing a density gradient having at least two layers of the composition according to claim 1, each layer having a different density;
separating the sperm sub-populations in the semen sample by centrifugation through the density gradient; and
selecting the sperm sub-population of interest.

12. The method according to claim 11, wherein the sperm sub-population is haploid spermatozoa from bull semen.

13. A method of artificial insemination, in vitro fertilization or intracytoplasmic sperm injection comprising:
obtaining spermatozoa by the method according to claim 2, and
delivering said spermatozoa.

14. A method of artificial insemination, in vitro fertilization or intracytoplasmic sperm injection comprising:
obtaining sperm by the method according to claim 11, and
delivering said sperm.

15. A composition for separating spermatozoa from a semen sample, the composition consisting of:
water;
97.5-140.0 mM of sodium chloride;
4.0-5.5 mM of potassium chloride;
1.0-1.4 mM of glucose;
0.10-0.14 mM of EDTA;
15.0-19.0 mM of HEPES;
4.8-8.3 mM of tri-sodium citrate;
0-4.0 mM of lactate;
0-2.7 mm of $CaCl_2$; and
300-1000 g/l of silane-coated silica particles,
wherein the composition has a pH of 7.0-7.35 and an osmolarity of 300-345 mOsm.

16. The composition according to claim 15, the $CaCl_2$ consisting of 2.5-2.7 mM of $CaCl_2$.

17. The composition according to claim 16, wherein the composition has an osmolarity of about 320-345 mOsm.

18. A method for preparing spermatozoa from a semen sample from a non-human animal, comprising separating the spermatozoa from other semen constituents by centrifugation through a single layer of a colloid formulation comprising the composition according to claim 15.

19. The method according to claim 18, wherein the colloid formulation has a density in the range of 1.05-1.14 g/ml, an osmolarity of about 320-330 mOsm, and a pH of 7.15-7.35.

20. A composition for separation of spermatozoa from a semen sample, the composition consisting of:
salt selected from the group consisting of alkali metal salts and alkaline earth metal salts,
glucose,
EDTA,
a zwitterion buffer,
citrate,
lactate,
silane-coated silica particles, and
water,
said composition having a pH of 7.0-7.35 and an osmolarity of 300-345 mOsm.

21. A method for preparing spermatozoa from a semen sample from a non-human animal, comprising separating the spermatozoa from other semen constituents by centrifugation through a single layer of a colloid formulation comprising the composition according to claim 20.

22. The method according to claim 21, wherein the colloid formulation has a density in the range of 1.05-1.14 g/ml.

23. The method according to claim 21, wherein the colloid formulation has a pH of 7.0-7.3.

24. The method according to claim 21, wherein the separation is performed in a container with a volume of 10 ml or more.

25. The method according to claim 24, wherein the separation is performed in a container with a volume of 50-200 ml.

26. The method according to claim 24, wherein the colloid composition is a 65-70% buffer dilution of a stock colloid formulation having a density of about 1.13-1.14 g/ml.

27. The method according to claim 21, wherein the colloid has a height of 30-45 mm.

28. The method according to claim 21, wherein the semen sample is not oligospermic.

29. The method according to claim 21, wherein the spermatozoa are separated from seminal plasma and its cellular or non-cellular components.

30. A method for separating a sperm sub-population of interest from a semen sample from a non-human animal, comprising:
providing a density gradient having at least two layers of the composition according to claim 20, each layer having a different density;
separating the sperm sub-populations in the semen sample by centrifugation through the density gradient; and
selecting the sperm sub-population of interest.

31. The method according to claim 30, wherein the sperm sub-population is haploid spermatozoa from bull semen.

32. A method of artificial insemination, in vitro fertilization or intracytoplasmic sperm injection comprising:
obtaining spermatozoa by the method according to claim 21, and
delivering said spermatozoa.

33. A method of artificial insemination, in vitro fertilization or intracytoplasmic sperm injection comprising:
obtaining sperm by the method according to claim 29, and
delivering said sperm.

* * * * *